US009532992B2

(12) United States Patent
Kuntz et al.

(10) Patent No.: US 9,532,992 B2
(45) Date of Patent: *Jan. 3, 2017

(54) SUBSTITUTED BENZENE COMPOUNDS

(71) Applicant: Epizyme, Inc., Cambridge, MA (US)

(72) Inventors: Kevin Wayne Kuntz, Woburn, MA (US); John Emmerson Campbell, Cambridge, MA (US); Masashi Seki, Tsukuba (JP)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,466

(22) Filed: Jun. 17, 2015

(65) Prior Publication Data

US 2015/0352119 A1 Dec. 10, 2015

Related U.S. Application Data

(63) Continuation of application No. 14/639,878, filed on Mar. 5, 2015, now Pat. No. 9,089,575, which is a continuation of application No. 14/054,695, filed on Oct. 15, 2013, now Pat. No. 9,006,242.

(60) Provisional application No. 61/714,140, filed on Oct. 15, 2012, provisional application No. 61/714,145, filed on Oct. 15, 2012, provisional application No. 61/780,703, filed on Mar. 13, 2013, provisional application No. 61/786,277, filed on Mar. 14, 2013.

(51) Int. Cl.
*A61K 31/5375* (2006.01)
*A61K 31/4545* (2006.01)
*A61K 31/4412* (2006.01)
*C07D 405/14* (2006.01)
*C07D 213/64* (2006.01)
*A61K 31/5377* (2006.01)
*C07D 401/12* (2006.01)
*C07D 405/12* (2006.01)

(52) U.S. Cl.
CPC ....... *A61K 31/5375* (2013.01); *A61K 31/4412* (2013.01); *A61K 31/4545* (2013.01); *A61K 31/5377* (2013.01); *C07D 213/64* (2013.01); *C07D 401/12* (2013.01); *C07D 405/12* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 5,716,993 A | 2/1998 | Ozaki et al. | |
| 5,948,803 A | 9/1999 | Maeda et al. | |
| 7,122,547 B1 | 10/2006 | Huth et al. | |
| 7,252,968 B2 | 8/2007 | Jenuwein et al. | |
| 7,442,685 B2 | 10/2008 | Zhang et al. | |
| 7,563,589 B2 | 7/2009 | Zhang et al. | |
| 7,923,219 B2 | 4/2011 | Wang et al. | |
| 8,410,088 B2 | 4/2013 | Kuntz et al. | |
| 8,754,230 B2 | 6/2014 | Livingston et al. | |
| 8,765,732 B2 | 7/2014 | Kuntz et al. | |
| 9,006,242 B2 | 4/2015 | Kuntz et al. | |
| 2002/0183324 A1 | 12/2002 | Jacobson et al. | |
| 2004/0082619 A1 | 4/2004 | Tada et al. | |
| 2005/0266473 A1 | 12/2005 | Zhang et al. | |
| 2008/0182844 A1 | 7/2008 | Bjergarde et al. | |
| 2008/0222741 A1 | 9/2008 | Chinnaiyan | |
| 2008/0269289 A1 | 10/2008 | Frank et al. | |
| 2008/0312292 A1 | 12/2008 | Yasui et al. | |
| 2009/0012031 A1 | 1/2009 | Chinnaiyan et al. | |
| 2009/0061443 A1 | 3/2009 | Zhang et al. | |
| 2009/0203057 A1 | 8/2009 | Zhang et al. | |
| 2010/0035912 A1 | 2/2010 | Debnath et al. | |
| 2010/0113415 A1 | 5/2010 | Rajapakse et al. | |
| 2011/0021362 A1 | 1/2011 | Trojer et al. | |
| 2012/0071418 A1 | 3/2012 | Copeland et al. | |
| 2013/0040906 A1 | 2/2013 | Kuntz et al. | |
| 2014/0142083 A1 | 5/2014 | Kuntz et al. | |
| 2014/0288041 A1 | 9/2014 | Kuntz et al. | |

FOREIGN PATENT DOCUMENTS

| | | |
|---|---|---|
| EP | 1357111 A1 | 10/2003 |
| JP | 7033729 A | 2/1995 |
| WO | WO 96/40100 A1 | 12/1996 |
| WO | WO 00/18725 A1 | 4/2000 |
| WO | WO 03/079788 A2 | 10/2003 |
| WO | WO 2006/116713 A1 | 11/2006 |
| WO | WO 2007/045462 A2 | 4/2007 |
| WO | WO 2007/050347 A1 | 5/2007 |
| WO | WO 2007/070818 A1 | 6/2007 |

(Continued)

OTHER PUBLICATIONS

Braña et al. "Reaction of N-(2-Pyridylmethyl)-3,5-dimethylbenzamide and N-(3-Pyridylmethyl)-3,5-dimethylbenzamide N-Oxides With Acetic Anhydride." *Journal of Heterocyclic Chemistry*, 19.6(1982):1297-1300.
Chemical Abstracts Service Registry Nos. 1111568-29-6, 1111508-57-6, and 1111473-93-8 entered Feb. 25, 2009.
Chemical Abstracts Service Registry Nos. 1118856-92-0, 1118847-80-5, 1118847-59-8, 1118826-65-5, 1118826-02-0, 1118825-96-9, 1118825-75-4, 1118825-72-1, and 1118825-69-6 entered Mar. 11, 2009.
Chemical Abstracts Service Registry Nos. 1278089-60-3, 1277914-52-9, and 1277529-83-5, entered Apr. 10, 2011.
Chemical Abstracts Service Registry Nos. 1278854-92-4 and 127885491-3, entered Apr. 12, 2011.
Chemical Abstracts Service Registry Nos. 919939-47-2 and 919873-05-5 entered Feb. 8, 2007.

(Continued)

*Primary Examiner* — Shirley V Gembeh
(74) *Attorney, Agent, or Firm* — Cooley LLP; Heidi A. Erlacher; Lian Ouyang

(57) ABSTRACT

The present invention relates to substituted benzene compounds. The present invention also relates to pharmaceutical compositions containing these compounds and methods of treating cancer by administering these compounds and pharmaceutical compositions to subjects in need thereof. The present invention also relates to the use of such compounds for research or other non-therapeutic purposes.

25 Claims, 4 Drawing Sheets

(56) References Cited

FOREIGN PATENT DOCUMENTS

| | | |
|---|---|---|
| WO | WO 2007/136592 A2 | 11/2007 |
| WO | WO 2008/073138 A2 | 6/2008 |
| WO | WO 2008/103277 A2 | 8/2008 |
| WO | WO 2008/104077 A1 | 9/2008 |
| WO | WO 2008/108825 A2 | 9/2008 |
| WO | WO 2008/113006 A1 | 9/2008 |
| WO | WO 2009/058298 A1 | 5/2009 |
| WO | WO 2009/077766 A1 | 6/2009 |
| WO | WO 2009/124137 A2 | 10/2009 |
| WO | WO 2010/018328 A1 | 2/2010 |
| WO | WO 2010/111653 A2 | 9/2010 |
| WO | WO 2011/082044 A1 | 7/2011 |
| WO | WO 2011/140324 A1 | 11/2011 |
| WO | WO 2011/140325 A1 | 11/2011 |
| WO | WO 2012/005805 A1 | 1/2012 |
| WO | WO 2012/034132 A2 | 3/2012 |
| WO | WO 2012/068589 A2 | 5/2012 |
| WO | WO 2012/075080 A1 | 6/2012 |
| WO | WO 2012/075500 A2 | 6/2012 |
| WO | WO 2012/118812 A2 | 9/2012 |
| WO | WO 2012/142504 A1 | 10/2012 |
| WO | WO 2012/142513 | 10/2012 |
| WO | WO 2013/138361 A1 | 9/2013 |
| WO | WO 2013/173441 A2 | 11/2013 |
| WO | WO 2014/062720 | 4/2014 |
| WO | WO 2014/062732 | 4/2014 |
| WO | WO 2014/062733 | 4/2014 |

OTHER PUBLICATIONS

Chemical Abstracts Service Registry Nos. 923162-97-4, 923152-74-3, and 923111-85-7 entered Feb. 26, 2007.
Chemical Abstracts Service Registry Nos. 923774-47-4, 923730-10-3, and 923690-12-4 entered Feb. 28, 2007.
Chemical Abstracts Service Registry Nos. 941139-86-2 and 941091-93-6 entered Jul. 4, 2007.
Gura et al. "Systems for Identifying New Drugs are Often Faulty." *Science*, 278.5340(1997):1041-1042.
Johnson et al. "Relationships Between Drug Activity in NCI Preclinical in vitro and in vivo Models and Early Clinical Trials." *Brit. J. Cancer*. 84.10(2001):1424-1431.
Knutson et al. "A Selective Inhibitor of EZH2 Blocks H3K27 Methylation and Kills Mutant Lymphoma Cells." *Nat. Chem. Biol.* (2012):1-7. Epub: Sep. 30, 2012.
Lohr et al. "Discovery and Prioritization of Somatic Mutations in Diffuse Large B-Cell Lymphoma (DLBCL) by Whole-Exome Sequencing." *PNAS*. 109.10(2012):3879-3884. Epub Feb. 17, 2012.
Martinez-Garcia et al. "The MMSET Histone Methyl Transferase Switches Global Histone Methylation and Alters Gene Expression in t(4;14) Multiple Myeloma Cells." *Blood*. 117(2011):211-220.
McCabe et al. "EZH2 Inhibition as a Therapeutic Strategy for Lymphoma With EZH2-Activating Mutations." *Nature*. Epub: Oct. 10, 2012.
McCabe et al. "Mutation of A677 in Histone Methyltransferase EZH2 in Human B-Cell Lymphoma Promotes Hypertrimethylation of Histone H3 on Lysine 27 (H3K27)." *PNAS*.109.8(2012):2989-2994.
Miranda et al. "DZNep is a Global Histone Methylation Inhibitor That Reactivates Developmental Genes not Silenced by DNA Methylation." *Mol. Cancer Ther*. 8.6(2009):1579-1588.
Morin et al. "Somatic Mutations Altering EZH2 (Tyr641) in Follicular and Diffuse Large B-Cell Lymphomas of Germinal-Center Origin." *Nat. Genet*. 42.2(2010):181-185.
Pearce et al. "Failure Modes in Anticancer Drug Discovery and Development." *Cancer Drug Design and Discovery*. Neidle, ed. Boston: Elsevier. (2008):424-435.
Sculley et al. "Some Amide Derivatives of Certain Aminomethylpyridines." *J. Am. Chem. Soc*. 75.14(1953):3400-3403.
Simone. "Oncology: Introduction." *Cecil Textbook of Medicine*. Bennett et al., eds. Philadelphia: W. B. Saunders Co. 20th ed. (Jan. 1996):1004-1008.
Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." *PNAS*. 107.49(2010):20980-20985.
Wigle et al. "The Y641 C Mutation of EZH2 Alters Substrate Specificity for Histone H3 Lysine 27 Methylation States." *FEBS Lett*. 585.19(2011):3011-3014.
Wilson et al. "Epigenetic Antagonism Between Polycomb and SWI/SNF Complexes During Oncogenic Transformation." *Cancer Cell*. 18(2010):316-328.
Yap et al. "Somatic Mutations at EZH2 Y641 Act Dominantly Through a Mechanism of Selectively Altered PRC2 Catalytic Activity, to Increase H3K27 Trimethylation." *Blood*. 117.8(2010):2451-2459.

US 9,532,992 B2

SUBSTITUTED BENZENE COMPOUNDS

RELATED APPLICATIONS

This application is a continuation of U.S. application Ser. No. 14/639,878, filed Mar. 5, 2015 (now allowed), which is a continuation of U.S. application Ser. No. 14/054,695, filed Oct. 15, 2013 (now U.S. Pat. No. 9,006,242), which claims priority to, and the benefit of, U.S. provisional application Nos. 61/714,140, filed Oct. 15, 2012, 61/714,145, filed Oct. 15, 2012, 61/780,703, filed Mar. 13, 2013, and 61/786,277, filed Mar. 14, 2013, the entire contents of each of which are incorporated herein by reference in their entireties.

INCORPORATION-BY-REFERENCE OF SEQUENCE LISTING

The contents of the text file named "EPIZ-014001US-ST25.txt", which was created on Feb. 5, 2015 and is 1.3 KB in size, are hereby incorporated by reference in their entireties.

BACKGROUND OF THE INVENTION

There is an ongoing need for new agents as inhibitors of EZH2 activity, which can be used for treating EZH2-mediated disorder (e.g., cancer).

SUMMARY OF THE INVENTION

In one aspect, the present invention features a substituted benzene compound selected from

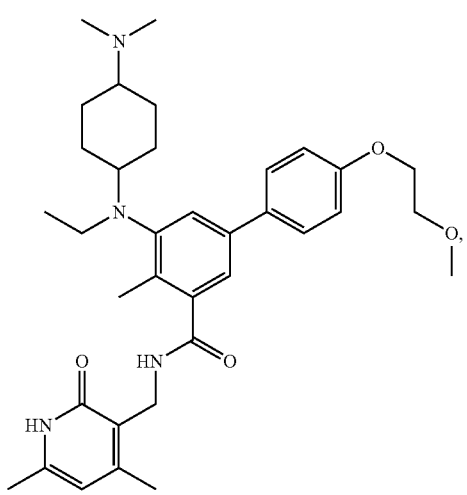

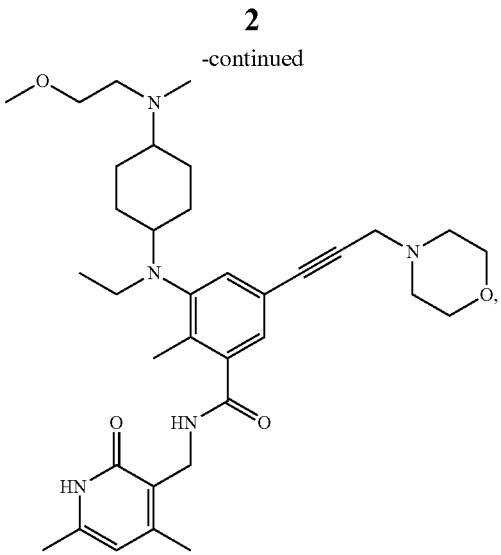

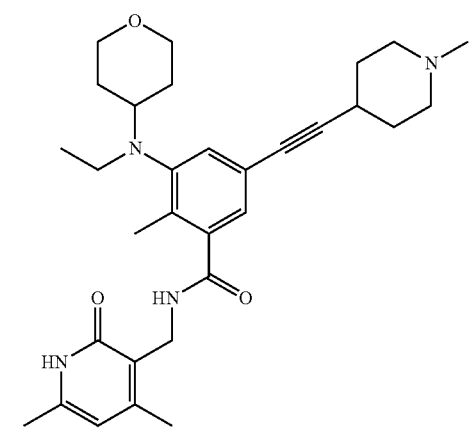

and pharmaceutically acceptable salts thereof.

For example, the compound is

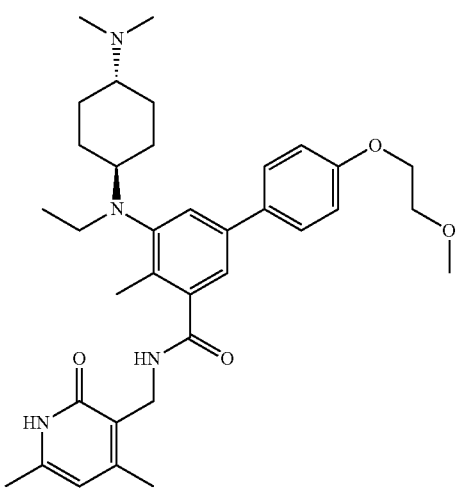

or a pharmaceutically acceptable salt thereof.

For example, the compound is

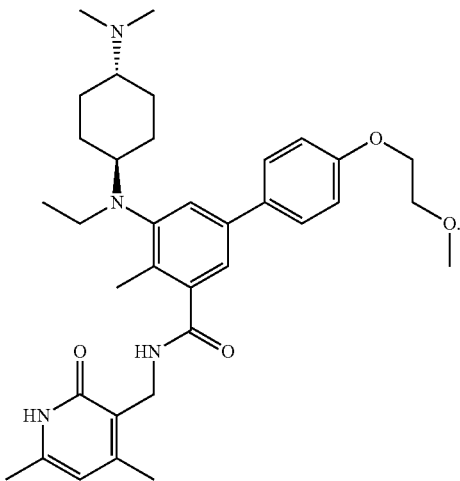

For example, the compound is

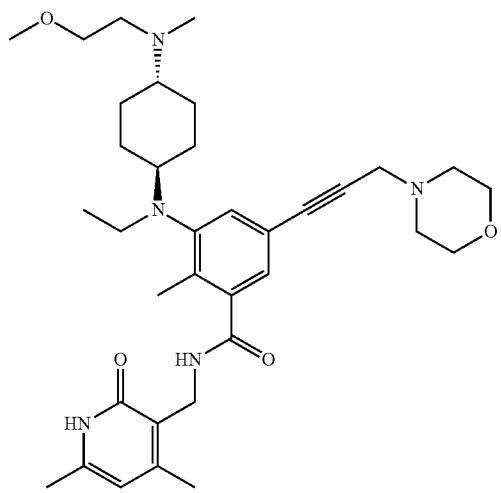 [SMILES: CCN(c1cc(C#CCN2CCOCC2)cc(C(=O)NCc2c(C)cc(C)[nH]c2=O)c1C)[C@H]1CC[C@H](N(C)CCOC)CC1]

or a pharmaceutically acceptable salt thereof
For example, the compound is

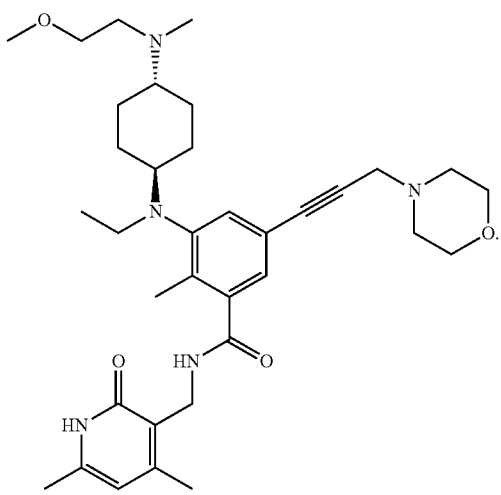

For example, the compound is

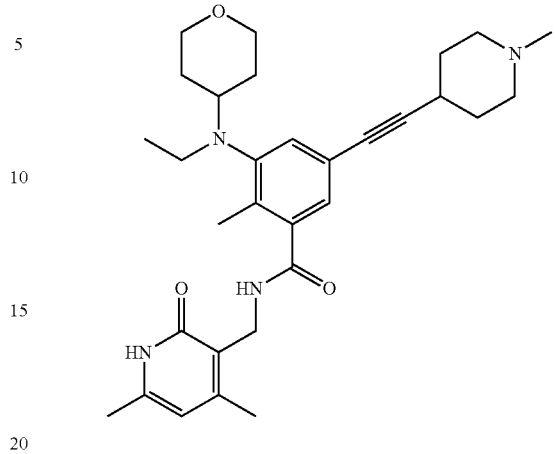

or a pharmaceutically acceptable salt thereof.
For example, the compound is

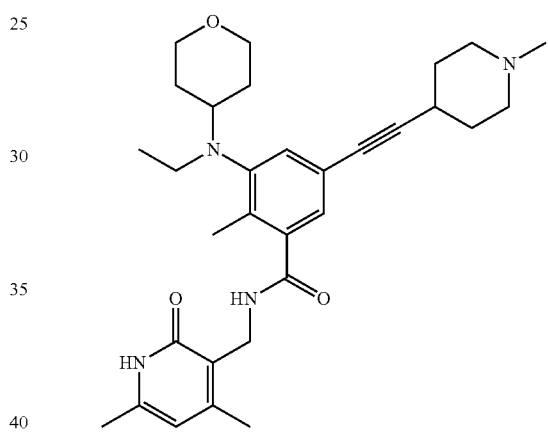

The present invention also provides pharmaceutical compositions comprising one or more pharmaceutically acceptable carriers and one or more compounds disclosed herein.

Another aspect of this invention is a method of treating or preventing an EZH2-mediated disorder. The method includes administering to a subject in need thereof a therapeutically effective amount of one or more compounds disclosed herein. The EZH2-mediated disorder is a disease, disorder, or condition that is mediated at least in part by the activity of EZH2. In one embodiment, the EZH2-mediated disorder is related to an increased EZH2 activity. In one embodiment, the EZH2-mediated disorder is a cancer. The EZH2-mediated cancer may be lymphoma, leukemia or melanoma, for example, diffuse large B-cell lymphoma (DLBCL), non-Hodgkin's lymphoma (NHL), follicular lymphoma, chronic myelogenous leukemia (CML), acute myeloid leukemia, acute lymphocytic leukemia, mixed lineage leukemia, or myelodysplastic syndromes (MDS). In one embodiment the EZH2-mediated cancer may be a malignant rhabdoid tumor or INI1-defecient tumor. The histologic diagnosis of malignant rhabdoid tumor depends on identification of characteristic rhabdoid cells (large cells with eccentrically located nuclei and abundant, eosinophilic cytoplasm) and immunohistochemistry with antibodies to vimentin, keratin and epithelial membrane antigen. In most malignant rhabdoid tumors, the SMARCB1/INI1 gene, located in chromosome band 22q11.2, is inactivated by deletions and/or mutations. In one embodiment, the malignant rhabdoid tumors may be INI1-defecient tumor.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models.

Further, the compounds or methods described herein may be used for research (e.g., studying epigenetic enzymes) and other non-therapeutic purposes.

In certain embodiments, the preferred compounds disclosed herein have desirable pharmacological and/or pharmacokinetic properties, e.g., low clearance rates and/or limited risk of adverse drug-drug interactions in combination therapy evaluated, for example, through time-dependent and reversible inhibition of cytochrome P-450 enzymes.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the invention will be apparent from the following detailed description and claims.

BRIEF DESCRIPTIONS OF FIGURES

Figure 3:
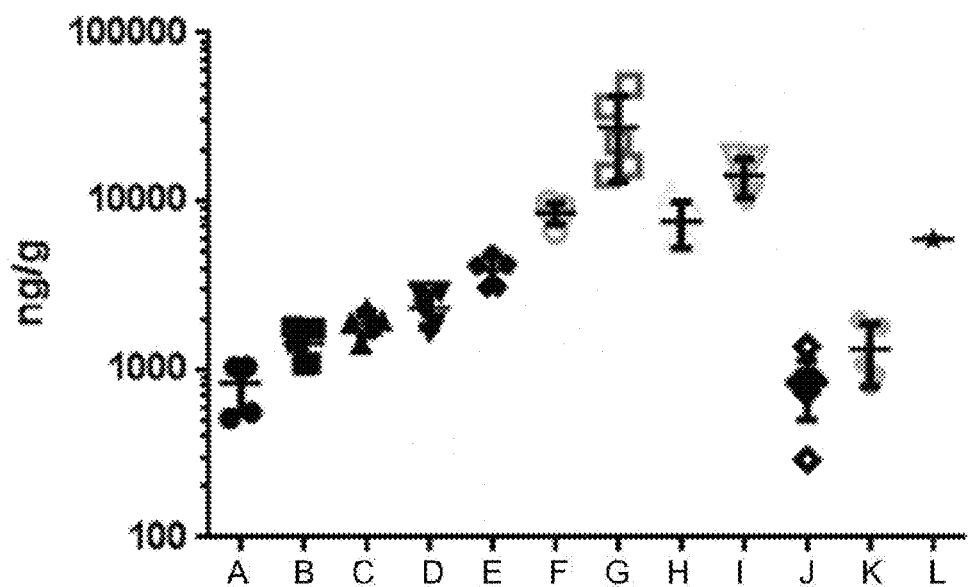

FIG. 3 is a diagram showing concentration of Compound 1 in tumor at day 7 or day 28 post treatment or concentration of Compound A in tumor at day 7 post treatment. In this figure, "A" though "G" denote 7 days post administration of Compound 1 at dosages of 62.5, 83.3, 125, 166.7, 250, 333.3, and 500 mg/kg, respectively; "H" and "I" denote 7 days post administration of Compound A at dosages of 125 and 250 mg/kg, respectively; and "J" through "L" denote 28 days post administration of Compound 1 at dosages of 62.5, 125 and 250 mg/kg, respectively.

Figure 4:
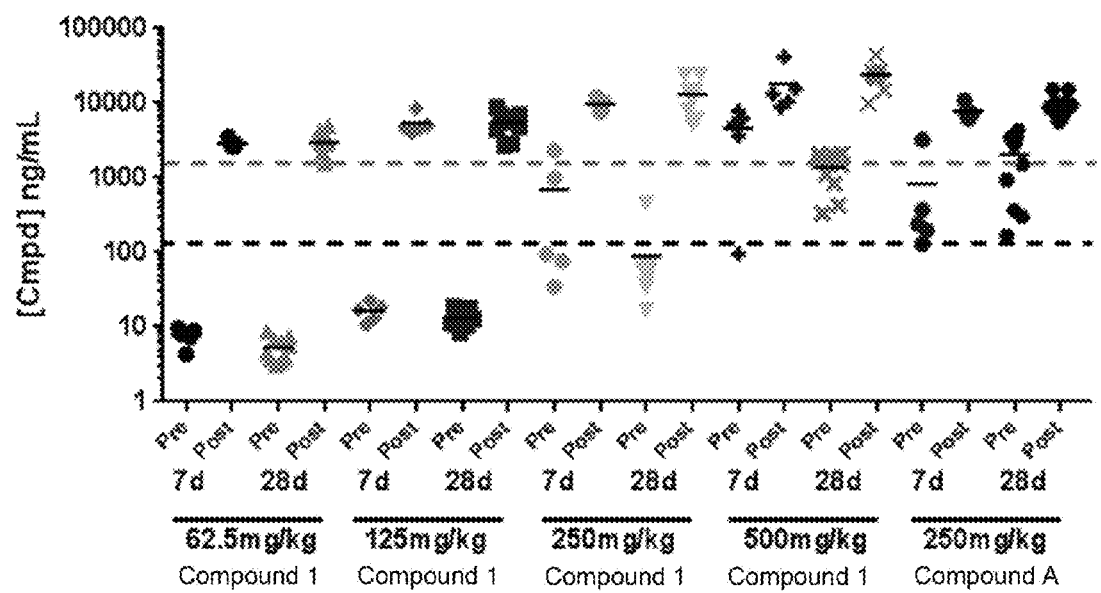

FIG. 4 is a diagram showing concentration of Compound 1 or Compound A in plasma at day 7 or day 28 post treatment. The top dashed line indicates the plasma protein binding (PPB) corrected LCC of Compound A and the bottom dashed line indicates PPB corrected LCC of Compound 1.

Figure 5:
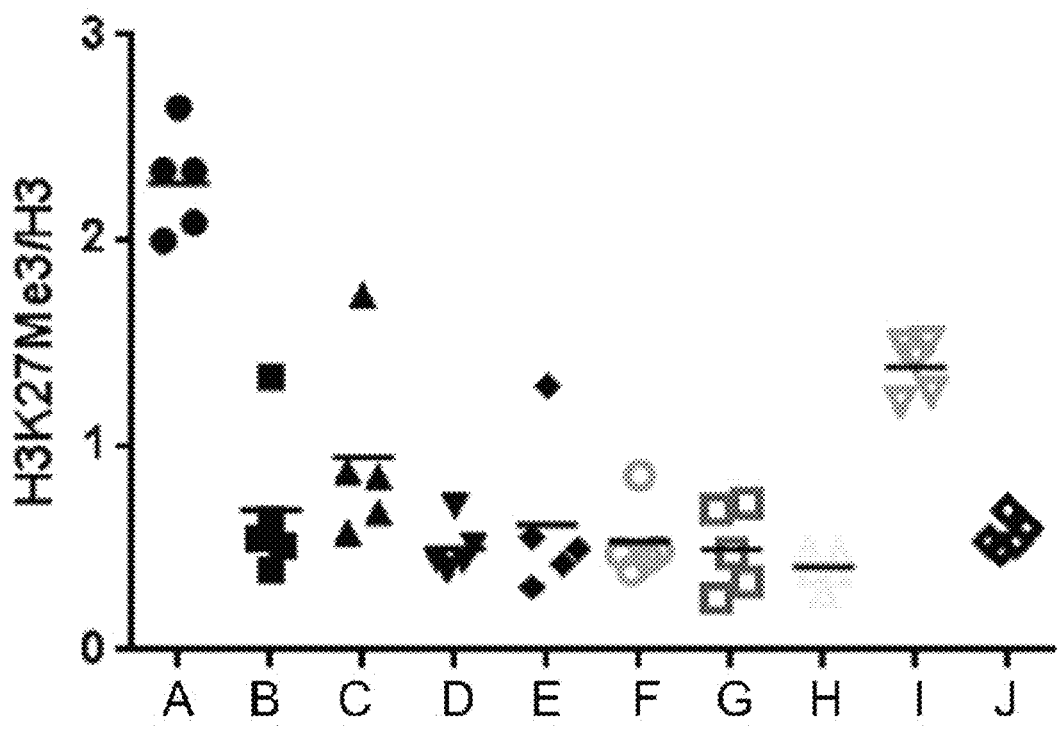

FIG. 5 is a diagram showing global H3K27me3 methylation in KARPAS-422 tumors from mice treated with Compound 1 or Compound A for 7 days. In this figure, "A" denotes vehicle treatment; "B" though "H" denote treatment with Compound 1 at dosages of 62.5, 83.3, 125, 166.7, 250, 333.3, and 500 mg/kg, respectively; and "I" and "J" denote treatment with Compound A at dosages of 125 and 250 mg/kg, respectively.

Figure 6:
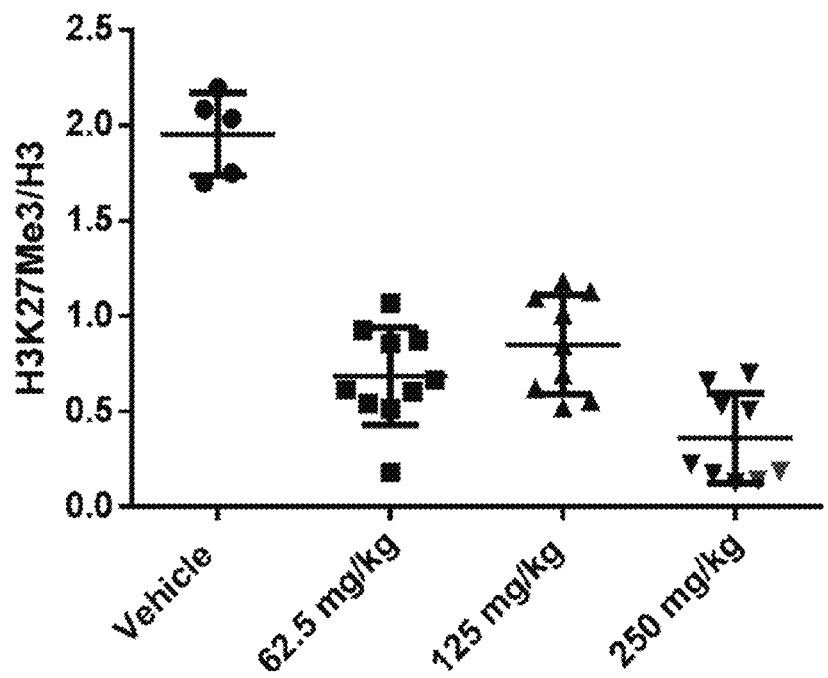

FIG. 6 is a diagram showing global H3K27me3 methylation in KARPAS-422 tumors from mice treated with Compound 1 for 28 days.

Figure 7:
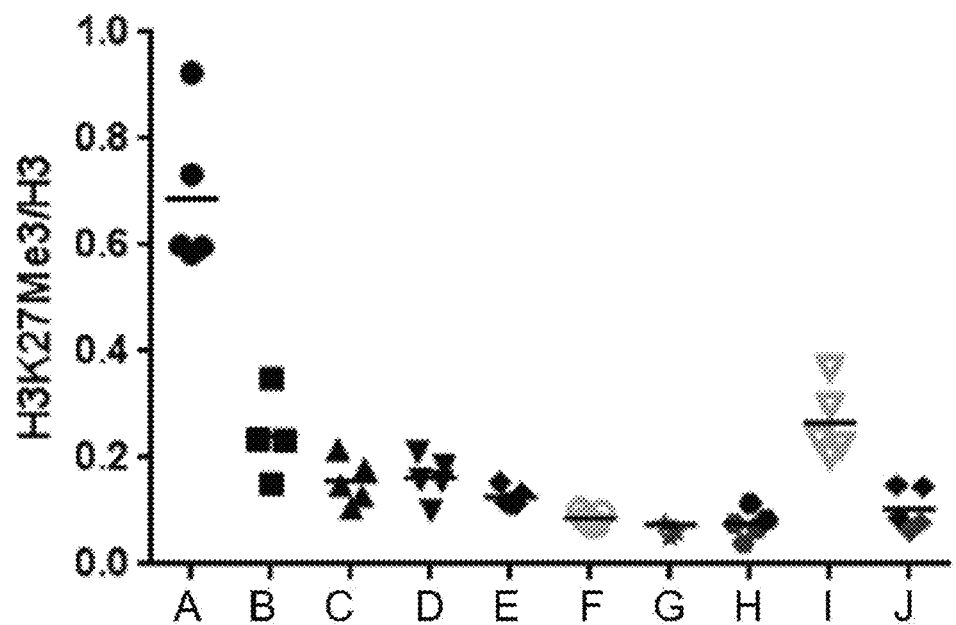

FIG. 7 is a diagram showing global H3K27me3 methylation in bone marrow from KARPAS-422 xenograft tumor bearing mice treated with Compound 1 or Compound A for 7 days. In this figure, "A" denotes vehicle treatment; "B" though "H" denote treatment with Compound 1 at dosages of 62.5, 83.3, 125, 166.7, 250, 333.3, and 500 mg/kg, respectively; and "I" and "J" denote treatment with Compound A at dosages of 125 and 250 mg/kg, respectively.

Figure 8:
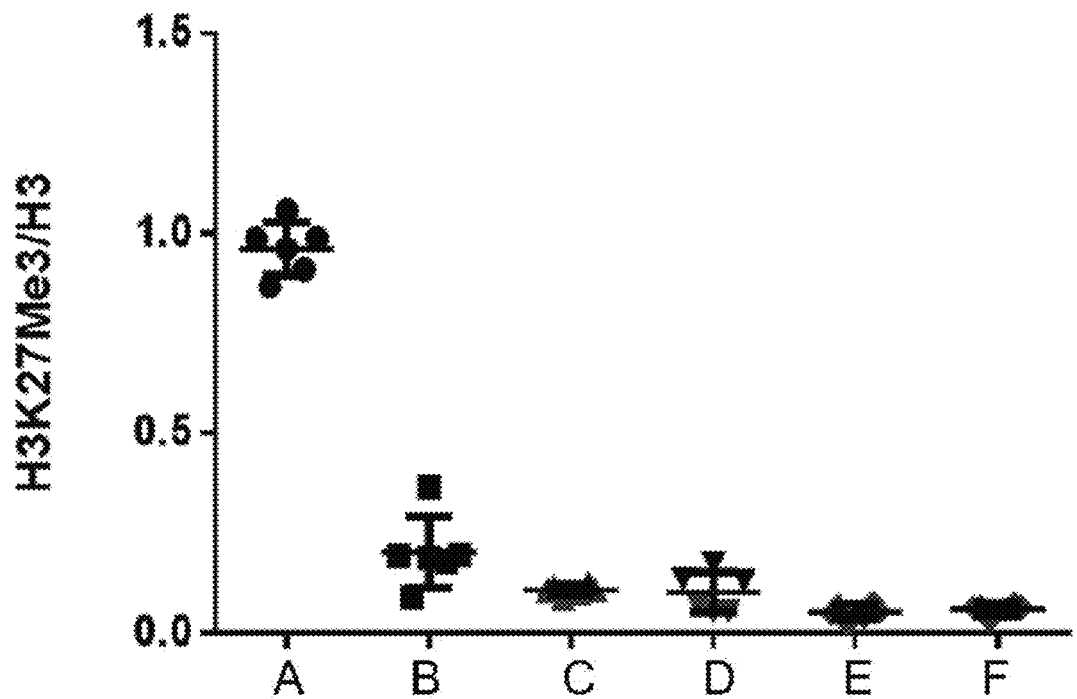

FIG. 8 is a diagram showing global H3K27me3 methylation in bone marrow from KARPAS-422 xenograft tumor bearing mice treated with Compound 1 for 28 days. In this figure, "A" denotes vehicle treatment; "B" though "E" denote treatment with Compound 1 at dosages of 62.5, 125, 250, and 500 mg/kg, respectively; and "F" denotes treatment with Compound A at a dosage of 250 mg/kg.

DETAILED DESCRIPTION OF THE INVENTION

The present invention provides novel substituted benzene compounds, synthetic methods for making the compounds, pharmaceutical compositions containing them and various uses of the compounds.

Representative compounds of the present invention include compounds listed in Table 1.

TABLE 1

| Compound no. | Structure |
|---|---|
| 1 | 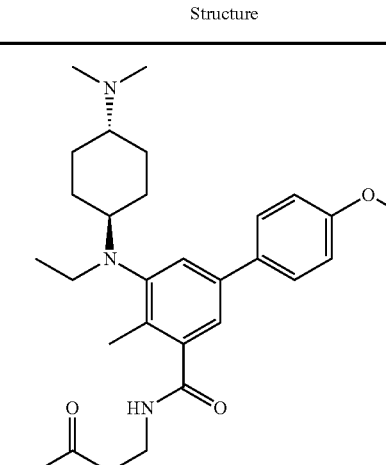 |

TABLE 1-continued

| Compound no. | Structure |
|---|---|
| 2 | (structure shown) |
| 105 | (structure shown) |

In the present specification, the structural formula of the compound represents a certain isomer for convenience in some cases, but the present invention may include all isomers, such as geometrical isomers, optical isomers based on an asymmetrical carbon, stereoisomers, tautomers, enantiomers, rotamers, diastereomers, racemates and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as stereoisomers. It should also be understood that when compounds have stereoisomeric forms, all stereoisomeric forms are intended to be included in the scope of the present invention, it being understood that not all stereoisomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

As used herein, any occurrence of

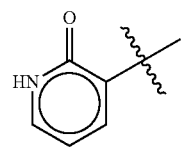

should be construed as

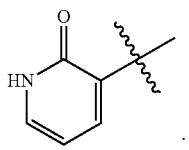

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

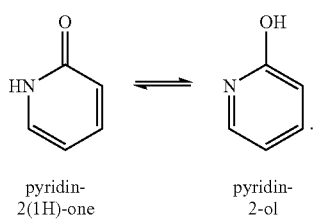 [SMILES: O=c1cccc[nH]1 ; Oc1ccccn1]

pyridin-2(1H)-one ⇌ pyridin-2-ol

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of this invention include the compounds themselves, such as any of the formulae disclosed herein. The compounds of this invention may also include their salts, and their solvates, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds in Table 1 are substituted benzene compounds, and have a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds disclosed herein. The present invention also provides detailed methods for the synthesis of various disclosed compounds of the present invention according to the schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps of older for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3$^{rd}$ edition, John Wiley & Sons: New York, 1999.

Preferred protecting groups include, but are not limited to:

For a hydroxyl moiety: TBS, benzyl, THP, Ac

For carboxylic acids: benzyl ester, methyl ester, ethyl ester, allyl ester

For amines: Cbz, BOC, DMB

For diols: Ac (×2) TBS (×2), or when taken together acetonides

For thiols: Ac

For benzimidazoles: SEM, benzyl, PMB, DMB

For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:

Ac acetyl
AcOH acetic acid
aq. aqueous
BID or b.i.d. bis in die (twice a day)
BOC tert-butoxy carbonyl
Cbz benzyloxy carbonyl
CDCl$_3$ deuterated chloroform
CH$_2$Cl$_2$ dichloromethane
DCM dichloromethane
DMB 2,4 dimethoxy benzyl
DMF N,N-Dimethylformamide
DMSO Dimethyl sulfoxide
EA or EtOAc Ethyl acetate
EDC or EDCI N-(3-Dimethylaminopropyl)-N'-ethylcarbodiimide
ESI−Electrospray negative mode
ESI+Electrospray positive mode
EtOH ethanol
h hours
H$_2$O water
HOBt 1-Hydroxybenzotriazole
HCl hydrogen chloride or hydrochloric acid
HPLC High performance liquid chromatography
K$_2$CO$_3$ potassium carbonate
LC/MS or LC-MS Liquid chromatography mass spectrum
M Molar
MeCN Acetonitrile
min minutes
Na$_2$CO$_3$ sodium carbonate
Na$_2$SO$_4$ sodium sulfate
NaHCO$_3$ sodium bicarbonate
NaHMDs Sodium hexamethyldisilazide
NaOH sodium hydroxide
NaHCO$_3$ sodium bicarbonate
Na$_2$SO$_4$ sodium sulfate
NMR Nuclear Magnetic Resonance
Pd(OH)$_2$ Palladium dihydroxide
PMB para methoxybenzyl
p.o. per os (oral adinsitration)
ppm parts per million
prep HPLC preparative High Performance Liquid Chromatography
PYBOP (Benzotriazol-1-yloxy)tripyrrolidinophosphonium hexafluorophosphate
Rt or RT Room temperature
TBME tert-Butyl methyl ether
TFA trifluoroacetic acid
THF tetrahydrofuran
THP tetrahydropyran Compounds of the present invention can be conveniently prepared by a variety of methods familiar to those skilled in the art. The compounds of this invention with any Formula disclosed herein may be prepared according to the procedures illustrated in the Examples below, from commercially available starting materials or starting materials which can be prepared using literature procedures.

One of ordinary skill in the art will note that, during the reaction sequences and synthetic schemes described herein, the order of certain steps may be changed, such as the introduction and removal of protecting groups.

Compounds of the present invention inhibit the histone methyltransferase activity of EZH2 or a mutant thereof and, accordingly, in one aspect of the invention, certain compounds disclosed herein are candidates for treating, or preventing certain conditions and diseases in which EZH2 plays a role. The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, polymorph, solvate, or stereoisomeror thereof.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models.

In still another aspect, this invention relates to a method of modulating the activity of the EZH2, the catalytic subunit of the PRC2 complex which catalyzes the mono- through tri-methylation of lysine 27 on histone H3 (H3-K27) in a subject in need thereof. For example, the method comprises the step of administering to a subject having a cancer expressing a mutant EZH2 a therapeutically effective amount of a compound described herein, wherein the compound(s) inhibits histone methyltransferase activity of EZH2, thereby treating the cancer.

For example, the EZH2-mediated cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin's lymphoma (NHL), follicular lymphoma or diffuse large B-cell lymphoma. Alternatively, the leukemia is chronic myelogenous leukemia (CML), acute myeloid leukemia, acute lymphocytic leukemia or mixed lineage leukemia.

For example, the EZH2-mediated precancerous condition is myelodysplastic syndromes (MDS, formerly known as preleukemia).

For example, the EZH2-mediated cancer is a hematological cancer.

The compound(s) of the present invention inhibit the histone methyltransferase activity of EZH2 or a mutant thereof and, accordingly, the present invention also provides methods for treating conditions and diseases the course of which can be influenced by modulating the methylation status of histones or other proteins, wherein said methylation status is mediated at least in part by the activity of EZH2. In one aspect of the invention, certain compounds disclosed herein are candidates for treating, or preventing certain conditions and diseases. Modulation of the methylation status of histones can in turn influence the level of expression of target genes activated by methylation, and/or target genes suppressed by methylation. The method includes administering to a subject in need of such treatment, a therapeutically effective amount of a compound of the present invention.

As used herein, a "subject" is interchangeable with a "subject in need thereof", both of which refer to a subject having a disorder in which EZH2-mediated protein methylation plays a part, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. A subject in need thereof can have refractory or resistant cancer (i.e., cancer that doesn't respond or hasn't yet responded to treatment). The subject may be resistant at start of treatment or may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In a preferred embodiment, the subject has cancer or a cancerous condition. For example, the cancer is lymphoma, leukemia, melanoma, or rhabdomyosarcoma. Preferably, the lymphoma is non-Hodgkin's lymphoma, follicular lymphoma or diffuse large B-cell lymphoma. Alternatively, the leukemia is chronic myelogenous leukemia (CML). The precancerous condition is myelodysplastic syndromes (MDS, formerly known as preleukemia).

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

Point mutations of the EZH2 gene at a single amino acid residue (e.g., Y641, A677, and A687) of EZH2 have been reported to be linked to lymphoma. More examples of EZH2 mutants and methods of detection of mutation and methods treatment of mutation-associated disorders are described in, e.g., U.S. Patent Application Publication No. US 20130040906, the entire content of which is incorporated herein by reference in its entirety.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

As used herein, "combination therapy" or "co-therapy" includes the administration of a compound of the present invention, or a pharmaceutically acceptable salt, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

The present invention also provides pharmaceutical compositions comprising a compound disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists.

It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes and chemical structures described herein, compounds may be drawn with one particular configuration (e.g., with or without a particular stereoisomer indicated) for simplicity. Such particular configurations or lack thereof are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Syntheses of Compounds of the Invention

General Experimental
NMR
$^1$H-NMR spectra were taken using $CDCl_3$ unless otherwise stated and were recorded at 400 or 500 MHz using a Varian or Oxford instruments magnet (500 MHz) instruments. Multiplicities indicated are s=singlet, d=doublet, t=triplet, q=quartet, quint=quintet, sxt=sextet, m=multiplet, dd=doublet of doublets, dt=doublet of triplets; br indicates a broad signal.

LCMS and HPLC

Mass: Waters Acquity Ultra Performance LC. HPLC: Products were analyzed by Shimadzu SPD-20A with 150× 4.5 mm YMC ODS-M80 column or 150×4.6 mm YMC-Pack Pro C18 column at 1.0 ml/min. Mobile phase was MeCN:$H_2O$=3:2 (containing 0.3% SDS and 0.05% $H_3PO_4$). Products were purified by HPLC/MS (MeOH—$H_2O$ containing 0.1% ammonium hydroxide) using Waters AutoPurification System with 3100 Mass Detector.

3-(Aminomethyl)-4,6-dimethyl-1,2-dihydropyridin-2-one HCl salt

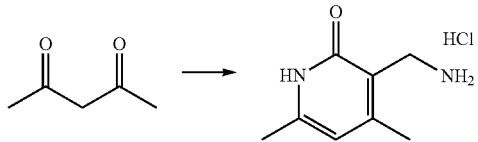

To a solution of 2-cyanoacetamide (8.40 g, 100 mmol) and acetylacetone (10.0 g, 100 mmol) in $H_2O$ (200 mL) was added $K_2CO_3$ (4.00 g, 28.9 mmol). The mixture was stirred at RT for 22 hours. Then the precipitated solid was filtered with Buchner funnel, washed with ice cold $H_2O$, and dried under vacuum pressure to give 4,6-dimethyl-2-oxo-1,2-dihydropyridine-3-carbonitrile (13.5 g, 91% yield).

To a solution of 4,6-dimethyl-2-oxo-1,2-dihydropyridine-3-carbonitrile (10.0 g, 67.5 mmol) in MeOH (1.50 L) and conc. HCl (30 mL) was added 10% Pd(OH)$_2$ (19 g) under $N_2$ atmosphere. The $N_2$ gas was displaced by $H_2$ gas and the mixture was stirred for 26 hours at RT under hydrogen atmosphere. The $H_2$ gas was displaced by $N_2$ gas. The mixture was filtered through Celite, washed with MeOH and concentrated. The residue was triturated with EtOH, collected with Buchner funnel, and dried under vacuum pressure to give the titled compound as a white solid (11.5 g, 90%). $^1$H NMR (400 MHz, DMSO-$d_6$): δ ppm 11.86 (brs, 1H), 5.98 (s, 1H), 3.78 (m, 2H), 2.20 (s, 3H), 2.16 (s, 3H).

5-Bromo-2-methyl-3-nitrobenzoic acid

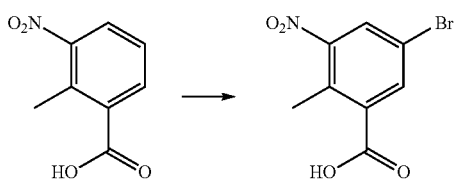

To a stirred solution of 2-methyl-3-nitrobenzoic acid (5.00 g, 27.6 mmol) in $H_2SO_4$ (20 mL) was added 1,3-dibromo-5,5-dimethylhydantoin (4.34 g, 15.20 mmol) at 0° C. The reaction mixture was stirred at 0° C. for 5 hours. The reaction mixture was poured onto ice cold water, the resultant precipitated solid was collected, washed with water and dried in vacuo to give the titled compound as a white solid (7.28 g, quantitative yield). $^1$H-NMR (400 MHz, DMSO-$d_6$) δ ppm; 8.31 (s, 1H), 8.17 (s, 1H), 2.43 (s, 3H).

Methyl 5-bromo-2-methyl-3-nitrobenzoate

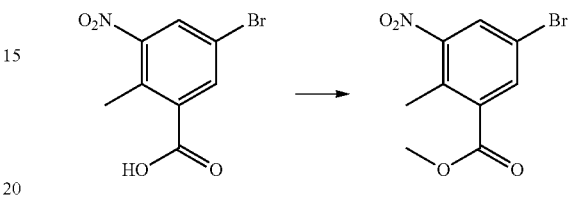

To a stirred solution of 5-bromo-2-methyl-3-nitrobenzoic acid (7.28 g, 28.0 mmol) in DMF (100 mL) was added sodium carbonate (11.9 g, 112 mmol) and methyl iodide (15.9 g, 112 mmol). The reaction mixture was stirred at 60° C. for 8 hours. After completion of the reaction, the reaction mixture was filtered and washed with ethyl acetate. The combined filtrate was washed with water and the aqueous phase was re-extracted with ethyl acetate. The combined organic layers were dried over anhydrous sodium sulfate, filtered and concentrated under reduced pressure to afford the titled compound as a solid. (7.74 g, quantitative yield). $^1$H-NMR (400 MHz, CDCl$_3$) δ (ppm); 8.17 (s, 1H), 7.91 (s, 1H), 3.96 (s, 3H), 2.59 (s, 3H).

Methyl 3-amino-5-bromo-2-methylbenzoate

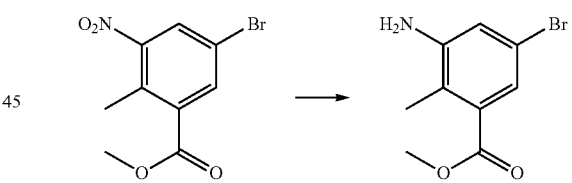

To a stirred solution of methyl 5-bromo-2-methyl-3-nitrobenzoate (7.60 g, 27.7 mmol) in aq. EtOH (100 mL of EtOH and 20 mL of $H_2O$) was added ammonium chloride (4.45 g, 83.1 mmol) and iron (4.64 g, 83.1 mmol). The reaction mixture was stirred at 80° C. for 5 hours. Then the mixture was filtered through Celite and the Celite bed was washed with ethyl acetate. The combined filtrate was concentrated in vacuo. The resultant residue was dissolved in ethyl acetate and water. The aqueous layer was extracted with ethyl acetate (twice). The combined organic layer dried over anhydrous sodium sulfate, filtered and concentrated under reduced pressure to afford the titled compound as a brown oil (6.67 g, 99%). $^1$H-NMR (400 MHz, CDCl$_3$) δ ppm; 7.37 (s, 1H), 6.92 (s, 1H), 3.94 (s, 3H), 3.80 (brs, 2H), 2.31 (s, 3H).

Compound 1

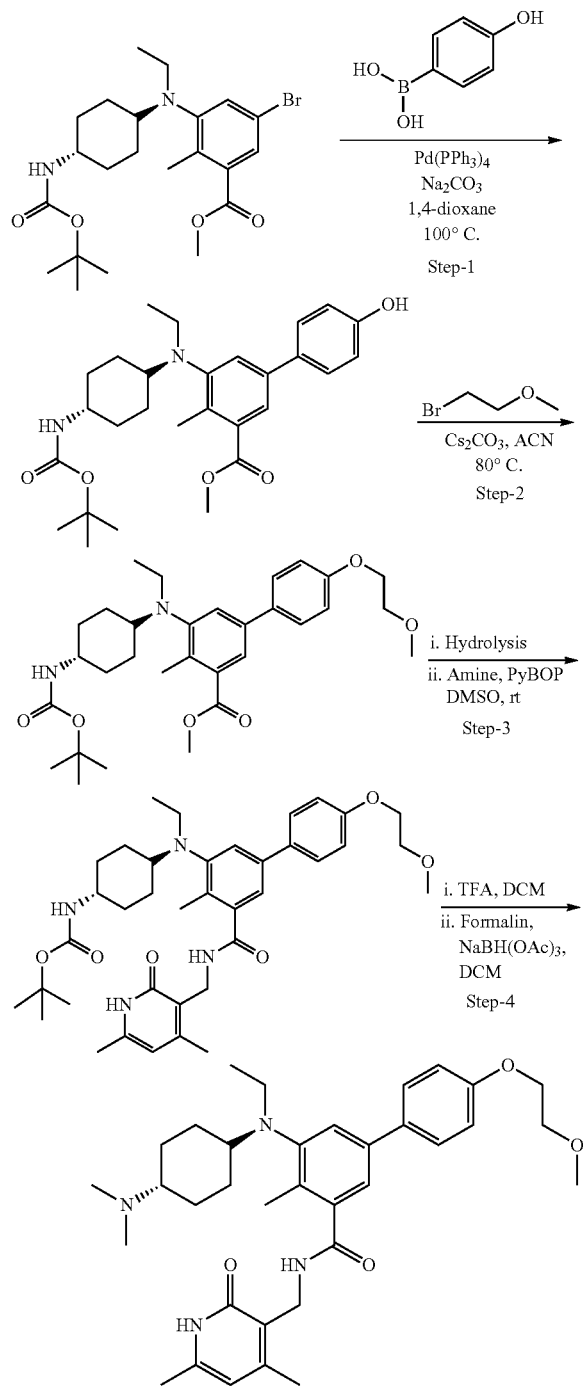

Step 1: Synthesis of methyl 5-(((trans)-4-((tert-butoxycarbonyeamino)cyclohexyl)(ethyl)amino)-4'-hydroxy-4-methyl-[1,1'-biphenyl]-3-carboxylate To a stirred solution of methyl 5-bromo-3-(((trans)-4-((tert-butoxycarbonyl)amino)cyclohexyl)(ethyl)amino)-2-methylbenzoate (10 g, 21.3 mmol, see, e.g., WO2012142504 (Attorney Docket No. 41478-507001WO)) and (4-hydroxyphenyl)boronic acid (3.5 g, 25.3 mmol) in a mixture of dioxane (225 mL) and water (75 mL), $Na_2CO_3$ (8.01 g, 75.5 mmol) was added and the solution was purged with argon for 30 min. Then $Pd(PPh_3)_4$ (2.4 g, 2.07 mmol) was added and argon was purged again for another 15 min. Reaction mass was heated at 100° C. for 4 h. On completion, reaction mixture was diluted with water and extracted with ethyl acetate. Combined organic layer was dried over sodium sulfate. Removal of the solvent under reduced pressure followed by column chromatographic purification afforded the title compound (8.9 g, 87% yield).

Step 2: Synthesis of methyl 5-(((trans)-4-((tert-butoxycarbonyl)amino) cyclohexyl)(ethyl)amino)-4'-(2-methoxyethoxy)-4-methyl-[1,1'-biphenyl]-3-carboxylate To a stirred solution of methyl 5-(((trans)-4-((tert-butoxycarbonypamino)cyclohexyl)(ethyl)amino)-4'-hydroxy-4-methyl-[1,1'-biphenyl]-3-carboxylate (0.6 g, 1.24 mmol) and 1-bromo-2-methoxyethane (0.519 g, 3.73 mmol) in acetonitrile (6 mL), $Cs_2CO_3$ (0.485 g, 1.49 mmol) was added and reaction was stirred at 80° C. for 12 h. On completion, water was added to it and extracted with ethyl acetate. The combined organic layers were dried over anhydrous sodium sulfate and concentrated under reduced pressure. The crude compound was purified by column chromatography to afford the title compound (0.6 g, 76.5% yield).

Step 3: Synthesis of tert-butyl ((trans)-4-((5-(((4,6-dimethyl-2-oxo-1,2-dihydropyridin-3-yl) methyl) carbamoyl)-4'-(2-methoxyethoxy)-4-methyl-[1,1'-biphenyl]-3-yl(ethyl)-amino)-cyclohexyl)carbamate Aqueous NaOH (0.066 g, 1.66 mmol in 5 mL $H_2O$) was added to a solution of methyl 5-(((trans)-4-((tert-butoxycarbonyl)amino)cyclohexyl)(ethyl)amino)-4'-(2-methoxyethoxy)-4-methyl-[1,1'-biphenyl]-3-carboxylate (0.6 g, 1.11 mmol) in EtOH (10 mL) and stirred at 60° C. for 1 h. After completion of the reaction, ethanol was removed under reduced pressure and the residue was acidified using citric acid using to pH 4 was adjusted using citric acid. Extraction was carried out using 10% methanol in DCM. Combined organic layers were dried, concentrated giving respective acid (0.5 g, 85.6% yield).

The above acid (0.5 g, 0.95 mmol) was then dissolved in DMSO (5 mL) and 3-(aminomethyl)-4,6-dimethylpyridin-2(1H)-one (0.288 g, 1.90 mmol) and triethyl amine (0.096 g, 0.950 mmol) was added to it. The reaction mixture was stirred at room temperature for 15 min before PyBop (0.741 g, 1.42 mmol) was added to it and stirring was continued for overnight at room temperature. After completion of the reaction, reaction mass was poured into ice and extraction was carried out using 10% MeOH/DCM. Combined organic layers were dried over sodium sulfate and concentrated under reduced pressure to obtain crude material which then purified by column chromatography to afford the title compound (0.45 g, 71.8% yield).

Step 4: Synthesis of N-((4,6-dimethyl-2-oxo-1,2-dihydropyridin-3-yl)methyl)-5-(((trans)-4-(dimethylamino)-cyclohexyl)(ethyl)-amino)-4'-(2-methoxyethoxy)-4-methyl-[1,1'-biphenyl]-3-carboxamide To a stirred solution of tert-butyl((trans)-4-((5-(((4,6-dimethyl-2-oxo-1,2-dihydropyridin-3-yl)methyl)carbamoyl)-4'-(2-methoxyethoxy)-4-methyl-[1,1'-biphenyl]-3-yl)(ethyl)amino)cyclohexyl)carbamate (0.45 g, 0.681 mmol) in DCM (5 mL) at 0° C., TFA (1 mL) was added and reaction was stirred for 2 h at room temperature. After completion, reaction was concentrated to dryness. The residue was then basified with $Na_2CO_3$ (aq.) to pH 8 and the aqueous layer extracted with 20% methanol in DCM. The combined organic layers were dried over $Na_2SO_4$ and the solvent removed under reduced pressure to give Boc-deprotected compound (0.3 g, 78.7% yield).

To a stirred solution of Boc-deprotected compound (0.3 g, 0.535 mmol) in dichloromethane (3 mL) was added formaldehyde solution (35-41% aq.) (0.056 g, 1.87 mmol) at 0° C. and stirred for 20 min. Then, $NaBH(OAc)_3$ (0.28 g, 1.33 mmol) was added and stirred for 2 h at 0° C. On completion of the reaction, water was added and extracted with 20% methanol in DCM. The combined organic layers were dried over $Na_2SO_4$ and the solvent was removed under reduced pressure. The crude compound was purified by prep. HPLC to afford the title compound (0.1 g, 31.7% yield).

LCMS: 589.75 (M+1)$^+$; TFA-salt: $^1$H NMR (DMSO-$d_6$, 400 MHz) δ 11.47 (brs, 1H), 9.48 (brs, 1H), 8.21 (brs, 1H), 7.57 (d, 2H, J=8.0 Hz), 7.40 (s, 1H), 7.23 (s, 1H), 7.03 (d, 2H, J=8.8 Hz), 5.87 (s, 1H), 4.29 (d, 2H, J=4.4 Hz), 4.14-4.12 (m, 2H), 3.69-3.66 (m, 2H), 3.32 (s, 3H), 3.13 (m, 4H), 2.69-2.68 (m, 6H), 2.24 (s, 3H), 2.21 (s, 3H), 2.11 (s, 3H), 1.96 (m, 4H), 1.44 (m, 4H), 0.85 (t, 3H, J=6.8 Hz).

Compound 2

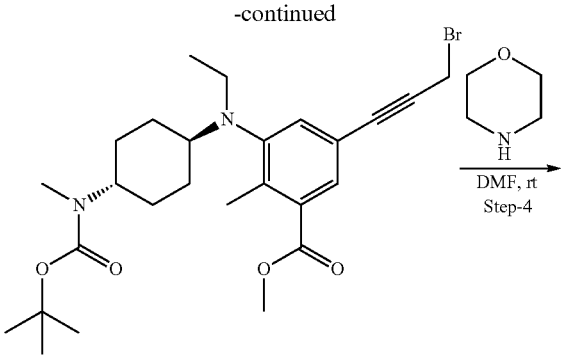
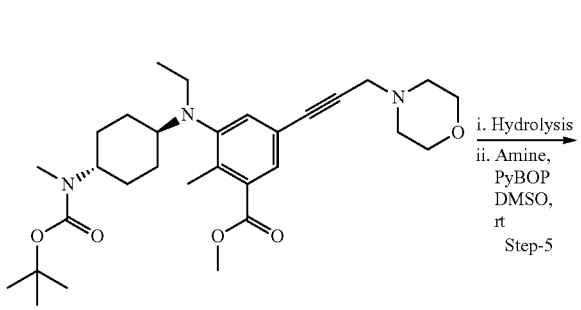
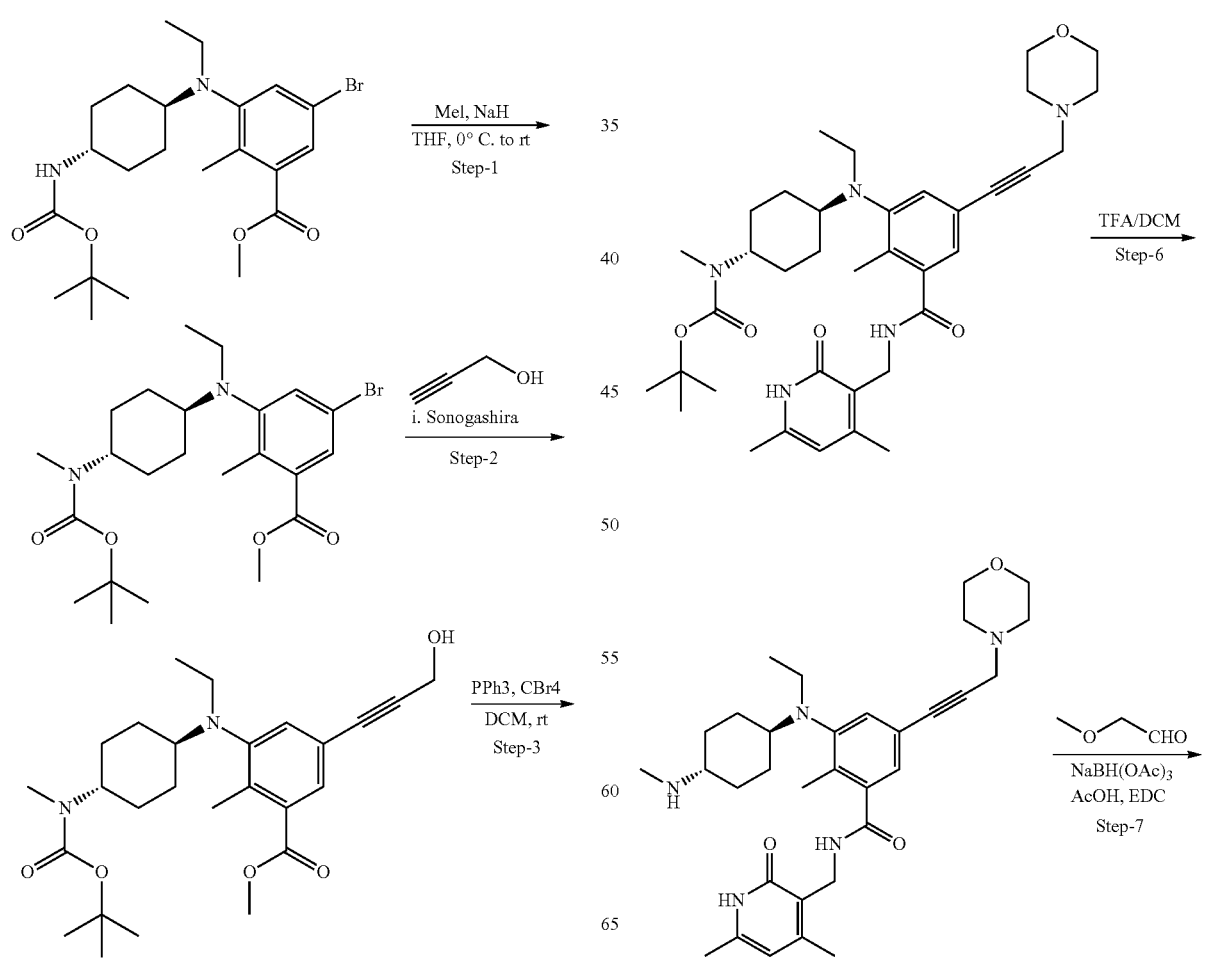

-continued

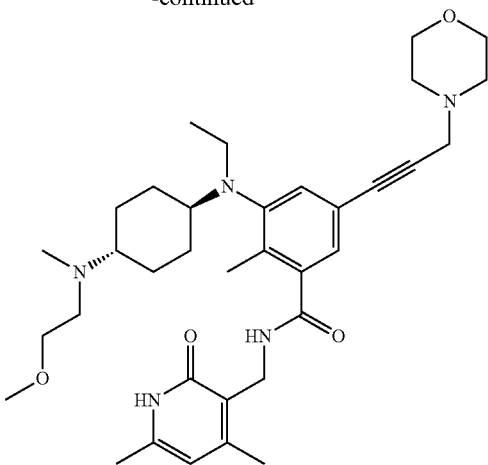

Step 1: Synthesis of methyl 5-bromo-3-(((trans) 4 ((tert-butoxycarbonyl)-(methyl)-amino)cyclohexyl)(ethyl)amino)-2-methylbenzoate To a stirred solution of methyl 5-bromo-3-(((trans)-4-((tert-butoxycarbonyl)amino)cyclohexyl)(ethyl)amino)-2-methylbenzoate (3 g, 6.41 mmol, see, e.g., WO2012142504) in THF (30 mL), NaH (0.184 g, 7.69 mmol) was added at 0° C. and stirred it at same temperature for 20 min. Then methyl iodide (9.10 g, 64.10 mmol) was added at 0° C. and reaction was stirred for overnight at room temperature. On completion, reaction was quenched with ice water and extracted with dichloromethane. The combined organic layers were washed with water, dried, concentrated under reduced pressure. The crude compound was purified by column chromatography to afford the crude title compound that was used without further purification (3 g, 97.4% yield).

Step 2: Synthesis of methyl 3-(((trans)-4-((tert-butoxycarbonyl)-(methyl)amino)cyclohexyl)(ethyl)amino)-5-(3-hydroxyprop-1-yn-1-yl)-2-methylbenzoate To a stirred solution of methyl 5-bromo-3-(((trans)-4-((tert-butoxycarbonyl)(methyl)amino)cyclohexyl)(ethyl)amino)-2-methylbenzoate (2 g, 4.14 mmol) in dry toluene was added CuI (0.015 g, 0.079 mmol), PPh$_3$ (0.043 g, 0.165 mmol), PdCl$_2$(PPh$_3$)$_2$ (0.058 g, 0.082 mmol), N,N-diisopropyl amine (1.08 g, 10.78 mmol) and reaction was purged with argon for 15 min. prop-2-yn-1-ol (0.46 g, 8.29 mmol) was added to it reaction was heated at 80° C. at sealed condition for 5 h. On completion, it was quenched with water and extracted with ethyl acetate. Organic layer was dried over Na$_2$SO$_4$. The crude compound was purified by column chromatography to afford the title compound (1.2 g, 63.2% yield).

Step 3: Synthesis of methyl 5-(3-bromoprop-1-yn-1-yl)-3-(((trans)-4-((tert-butoxy carbonyl)(methyl)amino)cyclohexyl)(ethyl)amino)-2-methylbenzoate To a stirred solution of methyl 3-(((trans)-4-((tert-butoxycarbonyl)(methyl)amino)cyclohexyl)(ethyl)amino)-5-(3-hydroxyprop-1-yn-1-yl)-2-methylbenzoate (1.2 g, 2.62 mmol) in DCM (15 mL), PPh$_3$ (1.37 g, 5.22 mmol) and CBr$_4$ (1.7 g, 5.10 mmol) were added at 0° C. and reaction was stirred for 4 h at room temperature. On Completion, reaction was quenched with ice water and extracted with dichloromethane. The combined organic layers were washed with water, dried, concentrated under reduced pressure. The crude material was purified by column chromatography to afford the title compound (0.5 g, 38.5% yield).

Step 4: Synthesis of methyl 3-(((trans)-4-((tert-butoxycarbonyl)(methyl)amino)cyclohexyl)(ethyl)amino)-2-methyl-5-(3-morpholinoprop-1-yn-1-yl)benzoate To a stirred solution of methyl 5-(3-bromoprop-1-yn-1-yl)-3-(((trans)-4-((tert-butoxy carbonyl)-(methyl)amino)cyclohexyl)(ethyl)amino)-2-methylbenzoate (1 equiv.) in DMF, morpholine (5 equiv.) was added and reaction was stirred for 12 h at room temperature. On completion, the reaction was quenched with ice water and extracted with dichloromethane. The combined organic layers were washed with water, dried, concentrated under reduced pressure to afford desired crude title compound that was used in the next step without further purification (98.7% yield)

Step 5: Synthesis of tert-butyl ((trans)-4-((3-(((4,6-dimethyl-2-oxo-1,2-dihydro pyridin-3-yl)methyl)carbamoyl)-2-methyl-5-(3-morpholinoprop-1-yn-1-yl)phenyl)(ethyl)amino)cyclohexyl)(methyl)carbamate NaOH (1.5 eq.) was added to a solution of methyl 3-(((trans)-4-((tert-butoxycarbonyl)(methyl)amino)cyclohexyl)(ethyl)amino)-2-methyl-5-(3-morpholinoprop-1-yn-1-yl)benzoate (1 equiv.) in EtOH:H$_2$O (9:1) and stirred at 60° C. for 1 h. After completion of the reaction, ethanol was removed under reduced pressure and acidified using dilute HCl up to pH 6 and pH 4 was adjusted using citric acid. Extraction was carried out using 10% methanol in DCM. Combined organic layers were dried concentrated giving respective acid.

The above acid (1 equiv.) was then dissolved in DMSO and 3-(aminomethyl)-4,6-dimethylpyridin-2(1H)-one (2 equiv.) and triethyl amine (1 equiv.) was added to it. The reaction mixture was stirred at room temperature for 15 min before PyBop (1.5 equiv.) was added to it and stirring was continued for overnight at room temperature. After completion of the reaction, the reaction mass was poured into ice and extraction was carried out using 10% MeOH/DCM. The combined organic layers were dried over Na$_2$SO$_4$ and concentrated under reduced pressure to obtain crude material which then purified first by water followed by acetonitrile washing to afford desired title compound (69.4% yield).

Step 6: Synthesis of N-((4,6-dimethyl-2-oxo-1,2-dihydropyridin-3-yl)methyl)-3-(ethyl((trans)-4-(methylamino)cyclohexyl)amino)-2-methyl-5-(3-morpholinoprop-1-yn-1-yl)benzamide To a stirred solution of tert-butyl((trans)-4-((3-(((4,6-dimethyl-2-oxo-1,2-dihydro pyridin-3-yl)methyl)carbamoyl)-2-methyl-5-(3-morpholinoprop-1-yn-1-yl) phenyl)(ethyl)amino)cyclohexyl)(methyl)carbamate (1 equiv.) in DCM at 0° C., TFA (3 equiv.) was added and reaction was stirred for 2 h at room temperature. After completion, reaction was concentrated to dryness. The residue was then basified with Na$_2$CO$_3$ (aq.) to pH 8 and the aqueous layer was extracted with 20% methanol in DCM. The combined organic layers were dried over Na$_2$SO$_4$ and solvent was removed under reduced pressure to afford the title compound (99% yield) which was used in the next reaction without further purification.

Step 7: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(3-morpholinoprop-1-yn-1-yl)benzamide To a stirred solution of N-((4,6-dimethyl-2-oxo-1,2-dihydropyridin-3-yl)methyl)-3-(ethyl((trans)-4-(methylamino)cyclohexyl)amino)-2-methyl-5-(3-morpholinoprop-1-yn-1-yl)benzamide (1 equiv.) in dichloroethane, 2-methoxyacetaldehyde (10 equiv.) and acetic acid (6 equiv.) was added at 0° C. and stirred for 20 min. Then NaBH(OAc)$_3$ (3 equiv.) was added and stirred for 2 h at 0° C. On completion of reaction, water was added and extracted with 20% methanol in DCM. Combined organic layers were dried over Na$_2$SO$_4$ and solvent removed under reduced pressure. The crude compound was purified by prep. HPLC to afford target molecule (0.1 g, 33.6% yield).

LCMS: 606.65 (M+1)$^+$; TFA salt: $^1$H NMR (DMSO-d$_6$, 400 MHz) δ 11.50 (brs, 1H), 9.22 (brs, 1H), 8.18 (t, 1H), 7.24 (s, 1H), 7.09 (s, 1H), 5.86 (s, 1H), 4.26-4.25 (m, 4H), 3.66-3.59 (m, 4H), 3.48-3.36 (m, 3H), 3.29-3.17 (m, 7H), 3.04-3.01 (m, 3H), 2.69-2.68 (m, 4H), 2.20 (s, 3H), 2.19 (s, 3H), 2.11 (s, 3H), 2.00-1.92 (m, 2H), 1.82-1.73 (m, 3H), 1.46 (m, 4H), 0.78 (t, 3H, J=6.4 Hz).

Alternative Synthetic Scheme for Compound 2

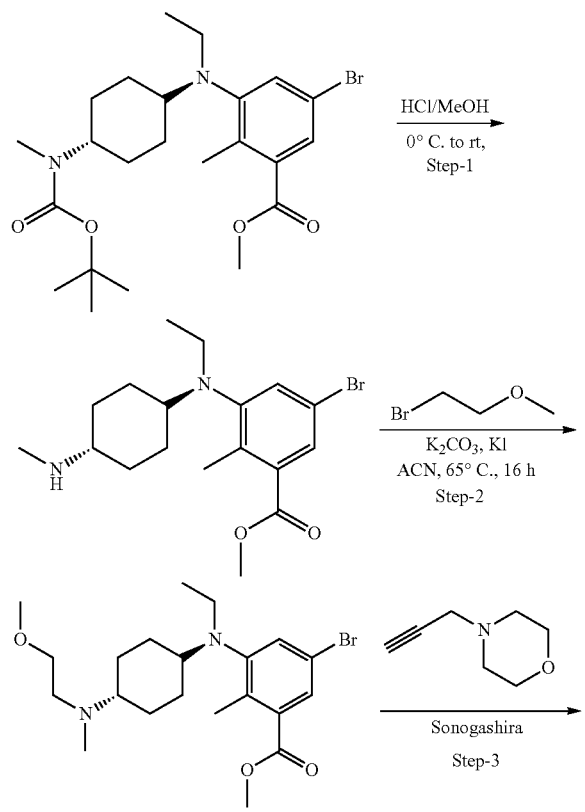

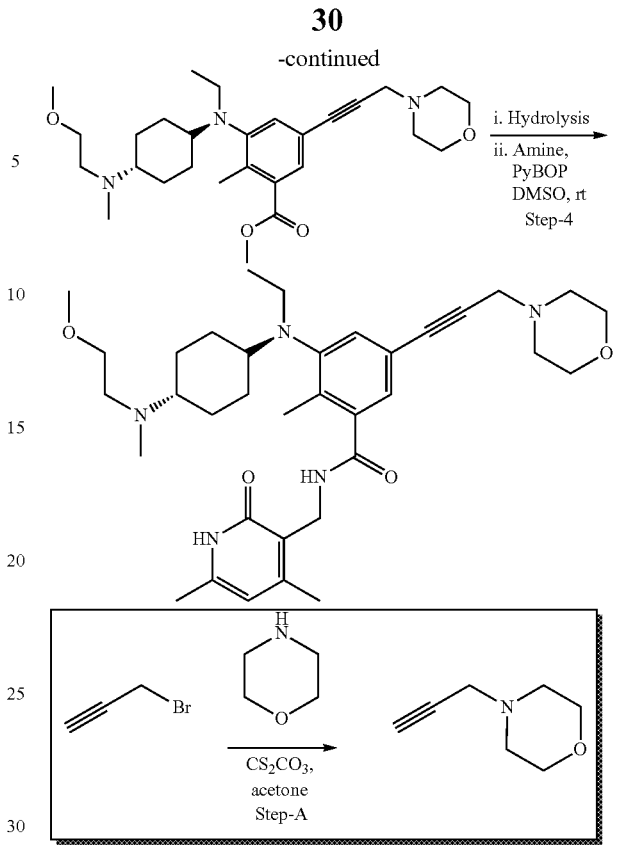

Step A: Synthesis of 4-(prop-2-yn-1-yl)morpholine

To a stirred solution of propargyl bromide (50 g, 420 mmol) in acetone (300 mL), Cs$_2$CO$_3$ (136.5 g, 420 mmol) was added at 0° C. Then morpholine (36.60 g, 420 mmol) in acetone (200 mL) was added dropwise and reaction was stirred at room temperature for 16 h. On completion, the reaction mass was filtered and the filtrate was concentrated under reduced pressure to afford the title compound (50 g, crude). The isolated compound was used directly in the subsequent coupling step without further purification.

Step 1: Synthesis of methyl 5-bromo-3-(ethyl((trans)-4-(methylamino)cyclohexyl)amino)-2-methylbenzoate To a stirred solution of methyl 5-bromo-3-(((trans)-4-((tert-butoxycarbonyl)(methyl)amino)cyclohexyl)(ethyl)amino)-2-methylbenzoate (30 g, 62.24 mmol) in methanol (100 mL) at 0° C., methanolic HCl (500 mL) was added and reaction was stirred for 2 h at room temperature. After completion, reaction was concentrated to dryness. The residue was basified with Na$_2$CO$_3$ (aq.) to pH 8 and aqueous layer was extracted with 10% methanol in DCM (200 mL×3). Combined organic layers were dried over Na$_2$SO$_4$ and solvent removed under reduced pressure to afford the title compound as colorless oil (25 g, crude). The isolated compound was used in the next step without further purification.

Step 2: Synthesis of methyl 5-bromo-3-(ethyl((trans)-4-((2-methoxyethyl)(methyl)amino)cyclohexyl)amino)-2-methylbenzoate To a stirred solution of crude methyl 5-bromo-3-(ethyl((trans)-4-(methylamino) cyclohexyl)amino)-2-methylbenzoate (25 g, 65.44 mmol), 1-bromo-2-methoxyethane (18.19 g, 130.8 mmol) in acetonitrile (250 mL), $K_2CO_3$ (18.06 g, 130.8 mmol) and KI (6.51 g, 39.21 mmol) were added. The resulting reaction mass was stirred at 65° C. for 16 h. On completion, reaction mixture was diluted with water (300 mL) and extracted with DCM (500 mL×3). The combined organic layers were washed with water, dried over $Na_2SO_4$ and concentrated under reduced pressure. The crude compound was purified by silica gel column chromatography to afford the title compound (20 g, 69.3% yield).

$^1$H NMR (DMSO-$d_6$, 400 MHz) δ 7.55 (s, 1H), 7.45 (s, 1H), 3.82 (s, 3H), 3.32 (m, 4H), 3.20 (s, 3H), 3.05 (q, 2H), 2.61 (m, 1H), 2.32 (s, 3H), 2.30 (m, 1H), 2.15 (s, 3H), 1.77-1.67 (m, 4H), 1.37-1.31 (m, 2H), 1.24-1.18 (m, 2H), 0.78 (t, 3H, J=6.8 Hz).

Step 3: Synthesis of methyl 3-(ethyl((trans)-4-((2-methoxyethyl)(methyl)amino)cyclohexyl)amino)-2-methyl-5-(3-morpholinoprop-1-yn-1-yl)benzoate To a solution of methyl 5-bromo-3-(ethyl((trans)-4-((2-methoxyethyl)(methyl)amino)cyclohexyl)amino)-2-methylbenzoate (30 g, 68.02 mmol), 4-(prop-2-yn-1-yl) morpholine (25.51 g, 204 mmol) and triethylamine (20.61 g, 204 mmol) in DMF (300 mL) was bubbled Argon for 20 min. Then CuI (3.87 g, 20.36 mmol) and Pd (PPh$_3$)$_4$ (7.85 g, 6.79 mmol) were added and Argon was bubbled through for further 20 min. The reaction mixture was heated at 105° C. for 4 h and then cooled to room temperature. The reaction was quenched with water (100 mL) and the aqueous phase was extracted with 10% MeOH/DCM (400 mL×3). The combined organic extracts were dried over $Na_2SO_4$, filtered and concentrated. The residue was purified by silica gel column chromatography to afford the title compound (21 g, 63.7% yield).

$^1$H NMR (DMSO-$d_6$, 400 MHz) δ 7.46 (s, 1H), 7.32 (s, 1H), 3.82 (s, 3H), 3.62-3.57 (m, 6H), 3.50 (s, 2H), 3.35-3.32 (m, 2H), 3.21 (s, 3H), 3.17 (m, 1H), 3.05 (q, 2H), 2.61-2.58 (m, 2H), 2.38 (s, 3H), 2.33 (m, 1H), 2.18 (m, 2H), 1.77-1.70 (m, 4H), 1.36-1.20 (m, 4H), 0.77 (t, 3H, J=6.8 Hz), 3H merged in solvent peak.

Step 4: Synthesis of N-((4,6-dimethyl-2-oxo-1,2-dihydropyridin-3-yl)methyl)-3-(ethyl((trans)-4-((2-methoxyethyl)(methyl)amino)cyclohexyl)amino)-2-methyl-5-(3-morpholinoprop-1-yn-1-yl)benzamide Aqueous NaOH (2.59 g, 64.91 mmol in 10 mL H$_2$O) was added to a solution of methyl 3-(ethyl((trans)-4-((2-methoxyethyl)(methyl)amino)cyclohexyl)amino)-2-methyl-5-(3-morpholinoprop-1-yn-1-yl)benzoate (21 g, 43.29 mmol) in EtOH (100 mL) and stirred at 60° C. for 1 h. After completion of the reaction, ethanol was removed under reduced pressure and the residue was acidified using dilute HCl up to pH 4 using citric acid. Extraction was carried out using 10% MeOH/DCM (200 mL×3). Combined organic layers were dried concentrated giving respective acid (15.5 g, 76% yield).

To the solution of above acid (15.5 g, 32.90 mmol) in DMSO (50 mL), 3-(aminomethyl)-4,6-dimethylpyridin-2 (1H)-one (10 g, 65.80 mmol) and triethyl amine (23 mL, 164.5 mmol) were added. The reaction mixture was stirred at room temperature for 15 min before PyBop (25.66 g, 49.34 mmol) was added to it at 0° C. and further stirred for overnight at room temperature. After completion, the reaction mass was poured into ice water (100 mL) and extraction was carried out using 10% MeOH/DCM (200 mL×3). Combined organic layers were dried over $Na_2SO_4$ and concentrated under reduced pressure. The crude compound was purified by column chromatography over basic alumina eluting with MeOH:DCM to afford the title compound (11 g, 55.3% yield).

LCMS: 606.50 (M+1)$^+$; $^1$H NMR (MeOD, 400 MHz) δ 7.23 (s, 1H), 7.09 (s, 1H), 6.11 (s, 1H), 4.46 (s, 2H), 3.74-3.72 (m, 4H), 3.51 (s, 2H), 3.47 (t, 2H, J=5.6 Hz,), 3.32 (s, 3H), 3.07 (q, 2H, J=7.2 Hz), 2.64-2.63 (m, 7H), 2.38 (m, 1H), 2.37 (s, 3H), 2.27 (s, 3H), 2.26 (s, 3H), 2.25 (s, 3H), 1.89-1.86 (m, 4H), 1.50-1.30 (m, 4H), 0.83 (t, 3H, J=7.2 Hz). cl Compound 105

Methyl 5-bromo-2-methyl-3-[(oxan-4-yl)amino]benzoate

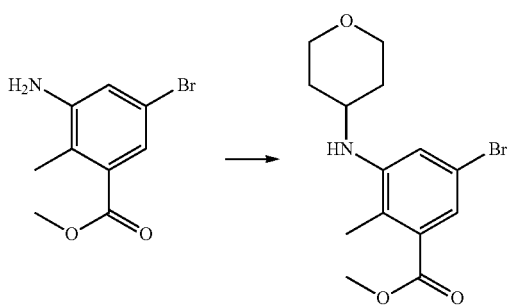 [SMILES: COC(=O)c1cc(Br)cc(N)c1C ; COC(=O)c1cc(Br)cc(NC2CCOCC2)c1C]

To a stirred solution of methyl 3-amino-5-bromo-2-methylbenzoate (40.2 g, 165 mmol) in CH$_2$Cl$_2$ (500 mL) and AcOH (60 mL) was added dihydro-2H-pyran-4-one (17.3 g, 173 mmol) and sodium triacetoxyborohydride (73.6 g, 330 mmol). The reaction mixture was stirred at RT for 20 hours. Then saturated NaHCO$_3$ aq. was added and the mixture was separated. The aqueous layer was extracted with CH$_2$Cl$_2$ and the combined organic layer was concentrated in vacuo. The residue was triturated with ethyl ether, and resultant precipitate was collected to afford the titled compound as a white solid (39.1 g, 72%). $^1$H-NMR (400 MHz, DMSO-$d_6$) δ ppm; 7.01 (s, 1H), 6.98 (s, 1H), 5.00 (d, J=7.6 Hz, 1H), 3.84-3.87 (m, 2H), 3.79 (s, 3H), 3.54-3.56 (m, 1H), 3.43 (m, 2H), 2.14 (s, 3H), 1.81-1.84 (m, 2H), 1.47-1.55 (m, 2H).

Methyl 5-bromo-3-[ethyl(oxan-4-yl)amino]-2-methylbenzoate

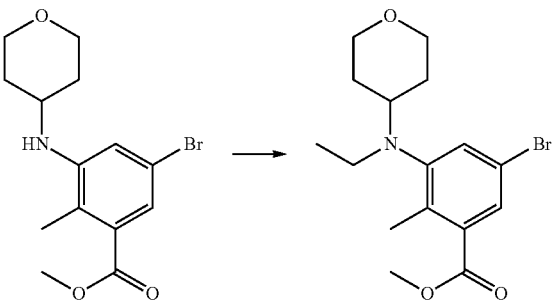 [SMILES: COC(=O)c1cc(Br)cc(NC2CCOCC2)c1C ; CCN(c1cc(Br)cc(C(=O)OC)c1C)C1CCOCC1]

To a stirred solution of methyl 5-bromo-2-methyl-3-[(oxan-4-yl)amino]benzoate (39.1 g, 119 mmol) in CH$_2$Cl$_2$ (400 mL) and AcOH (40 mL) was added acetaldehyde (24.7 g, 476 mmol) and sodium triacetoxyborohydride (79.6 g, 357 mmol). The reaction mixture was stirred at RT for 24 hours. Then saturated NaHCO$_3$ aq. was added and the mixture was separated. The aqueous layer was extracted with CH$_2$Cl$_2$ and the combined organic layer was concentrated in vacuo. The residue was purified by silica gel column chromatography (SiO$_2$ Heptane/EtOAc=3/1) to give the titled compound as a viscous oil (44.1 g, quantitative yield). $^1$H-NMR (400 MHz, DMSO-d$_6$) δ ppm; 7.62 (s, 1H), 7.52 (s, 1H), 3.80 (m, 5H), 3.31 (m, 2H), 2.97-3.05 (m, 2H), 2.87-2.96 (m, 1H), 2.38 (s, 3H), 1.52-1.61 (m, 2H), 1.37-1.50 (m, 2H), 0.87 (t, J=6.8 Hz, 3H).

tert-Butyl 4-((3-(ethyl(tetrahydro-2H-pyran-4-yl) amino)-5-(methoxycarbonyl)-4-methylphenyl)ethy- nyl)piperidine-1-carboxylate

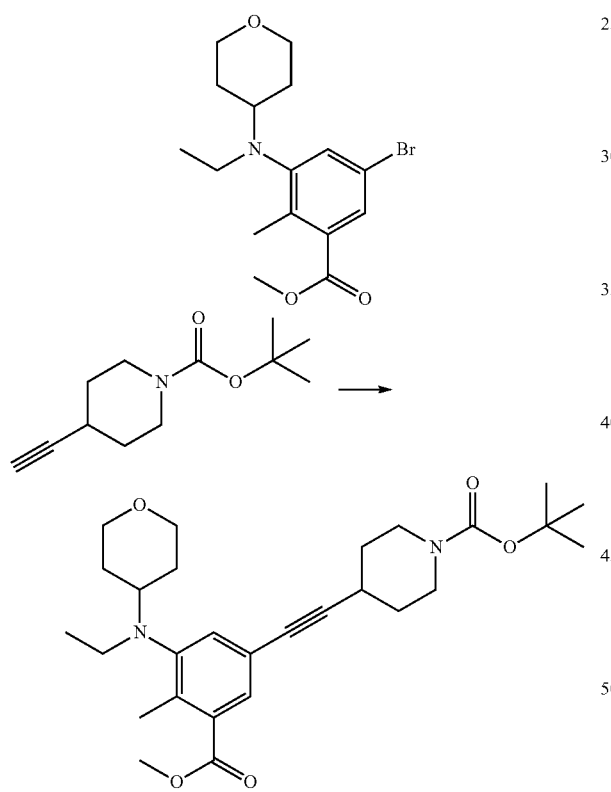

To a solution of methyl 5-bromo-3-(ethyl(tetrahydro-2H-pyran-4-yl)amino)-2-methylbenzoate (1.80 g, 5.05 mmol) and tert-butyl 4-ethynylpiperidine-1-carboxylate (1.80 g, 8.59 mmol) in DMF (40 ml) was added triethylamine (2.82 ml, 20.2 mmol) and Copper(I) iodide (0.096 g, 0.505 mmol). The reaction mixture was degassed by bubbling nitrogen for 15 min. Then tetrakis(triphenylphosphine)palladium(0) (0.292 g, 0.253 mmol) was introduced and degassed for additional 10 min by bubbling nitrogen. The reaction mixture was heated at 80° C. for 6 h. The reaction was quenched with sat. NaHCO3, extracted with TBME (3×40 mL), dried over Na2SO4, filtered and concentrated. The residue was purified by chromatography (0% to 40% AcOEt/Heptane) to give the titled compound (2.40 g, 98% yield). $^1$H-NMR (500 MHz) δ ppm; 7.65 (s, 1H), 7.28 (s, 1H), 3.97 (brd, J=11.3 Hz, 2H), 3.90 (s, 3H), 3.76 (m, 2H), 3.34 (dt, J=2.0, 11.7 Hz, 2H), 3.24 (ddd, J=3.4, 8.8, 12.2 Hz, 2H), 3.08 (brs, 2H), 2.98 (brs, 1H), 2.80 (dddd, J=3.9, 3.9, 3.9, 3.9 Hz, 1H), 2.52 (s, 3H), 1.87 (m, 2H), 1.60-1.74 (m, 6H), 1.48 (s, 9H), 0.89 (t, J=6.8 Hz, 3H)); MS (ESI) [M+H]$^+$ 485.4.

5-((1-(tert:Butoxycarbonyl)piperidin-4-yl)ethynyl)- 3-(ethyl(tetrahydro-2H-pyran-4-yl)amino)-2-methyl- benzoic acid

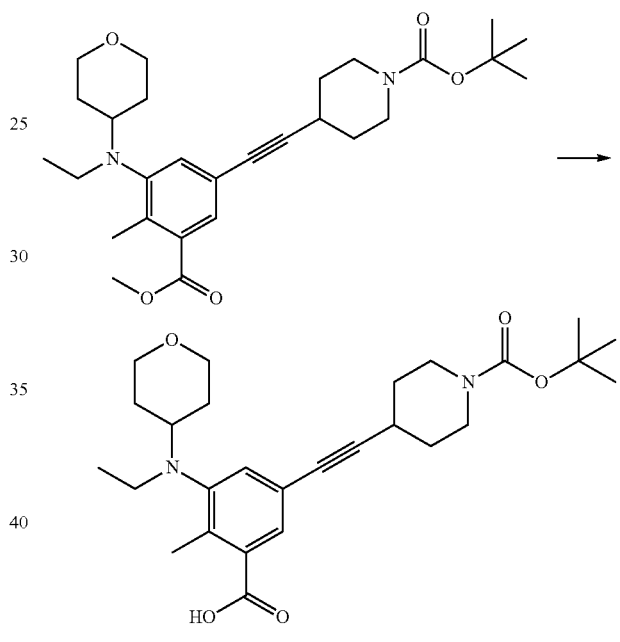

To a solution of tert-butyl 4-((3-(ethyl(tetrahydro-2H-pyran-4-yl)amino)-5-(methoxycarbonyl)-4-methylpheny- eethynyl)piperidine-1-carboxylate (2.4 g, 4.95 mmol) in ethanol (20.0 mL) was added a solution of sodium hydroxide (0.565 g, 14.1 mmol) in water (3.0 ml) at rt. The reaction mixture was heated at 60° C. for 6 h. The reaction was quenched with 1 M HCl (5 mL) and then excess citric acid solution to adjust to the pH to 5. The mixture was concentrated to remove EtOH and the remaining aqueous phase was extracted with AcOEt (2×40 mL). The organic layers were combined, dried over Na$_2$SO$_4$, filtered and concentrated. The residue was purified by chromatography (10%-100% AcOEt/Heptane) to give the titled compound (2.30 g, 99% yield). $^1$H-NMR (500 MHz) δ ppm; 7.82 (s, 1H), 7.35 (s, 1H), 3.98 (brd, J=11.3 Hz, 2H), 3.77 (m, 2H), 3.35 (dt, J=1.5, 11.3 Hz, 2H), 3.25 (ddd, J=3.4, 8.3, 12.2 Hz, 2H), 3.11 (brs, 2H), 3.00 (brs, 1H), 2.81 (dddd, J=3.9, 3.9, 3.9, 3.9 Hz, 1H), 2.60 (s, 3H), 1.88 (m, 2H), 1.60-1.78 (m, 6H), 1.48 (s, 9H), 0.90 (t, J=6.8 Hz, 3H); MS (ESI) [M+H]$^+$471.4.

35 tert-Butyl 4-((3-(((4,6-dimethyl-2-oxo-1,2-dihydro-pyridin-3-yl)methyl)carbamoyl)-5-(ethyl(tetrahydro-2H-pyran-4-yl)amino)-4-methylphenyl)ethynyl)piperidine-1-carboxylate

36

N-((4,6-Dimethyl-2-oxo-1,2-dihydropyridin-3-yl)methyl)-3-(ethyl(tetrahydro-2H-pyran-4-yl)amino)-2-methyl-5-(piperidin-4-ylethynyl)benzamide

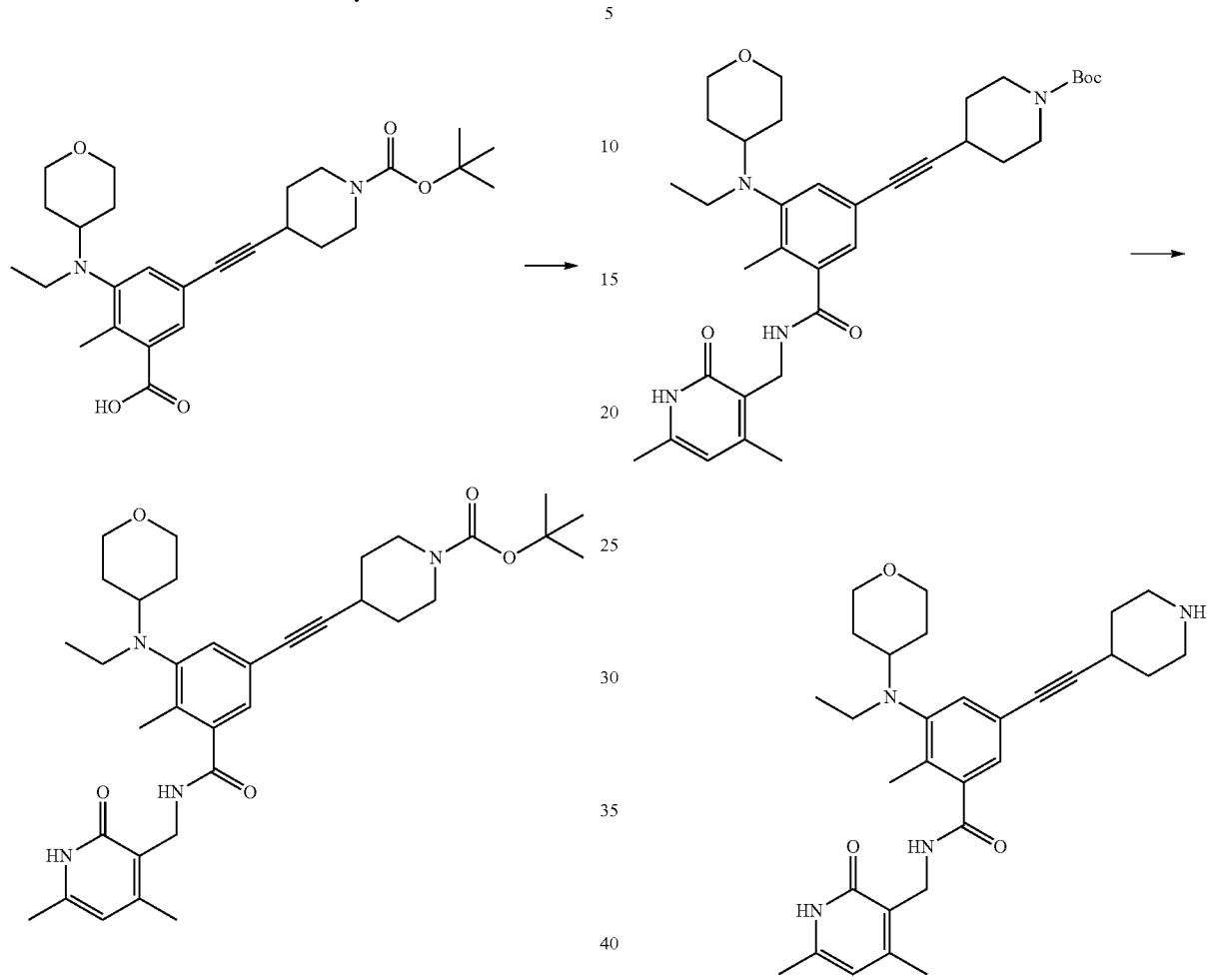

To a solution of 5-((1-(tert-butoxycarbonyl)piperidin-4-yl)ethynyl)-3-(ethyl(tetrahydro-2H-pyran-4-yl)amino)-2-methylbenzoic acid (1.06 g, 2.25 mmol) in DMSO (5.8 mL) at rt was added triethylamine (0.90 mL, 6.44 mmol) and (4,6-dimethyl-2-oxo-1,2-dihydropyridin-3-yl)methanaminium chloride (0.405 g, 2.15 mmol). The clear solution become heterogenous. Then HOBT (0.493 g, 3.22 mmol) and EDC (0.617 g, 3.22 mmol) were added and the resulting reaction mixture was stirred at rt overnight. The reaction was quenched with water (80 mL) and the slurry was stirred for 1 h at rt. The slurry was filtrated and the cake was washed with water (2×20 mL). The collected solid was dried under vacuum to give the titled compound (1.27 g, 98% yield). $^{1}$H-NMR (500 MHz, CD$_3$OD) δ ppm; 7.22 (s, 1H), 7.08 (d, J=1.0 Hz 1H), 6.11 (s, 1H), 4.45 (s, 2H), 3.92 (brd, J=10.8 Hz, 2H), 3.78 (dd, J=4.4, 5.4 Hz, 1H), 3.75 (dd, J=4.4, 5.4 Hz, 1H), 3.36 (t, J=11.7 Hz, 2H), 3.21 (br t, J=8.3 Hz, 2H), 3.07 (q, J=7.3 Hz, 2H), 3.01 (dddd, J=3.9, 3.9, 11.3, 11.3 Hz, 1H), 2.84 (dddd, J=3.4, 3.4, 3.9, 3.9 Hz, 1H), 2.38 (s, 3H), 2.28 (s, 3H), 2.25 (s, 3H), 1.88 (m, 2H), 1.70 ((brd, J=12.2 Hz, 2H), 1.60 (m, 4H), 1.47 (s, 9H), 0.87 (t, J=7.3 Hz, 3H); MS (ESI) [M+H]$^+$ 605.6.

To a solution of tert-butyl 4-((3-(((4,6-dimethyl-2-oxo-1,2-dihydropyridin-3-yl)methyl)carbamoyl)-5-(ethyl(tetrahydro-2H-pyran-4-yl)amino)-4-methylphenyl)ethynyl)piperidine-1-carboxylate (250 mg, 0.413 mmol) in DCM (3 mL) was added 4M HCl in 1,4-dioxane (3 mL, 12.0 mmol) at 20° C. The mixture was stirred at 20° C. for 1 h. LCMS indicated that the reaction was completed. The reaction mixture was directly concentrated and the residue was dissolved in DCM and then neutralized with sat. NaHCO$_3$/brine. The organic layer was dried (Na$_2$SO$_4$) and filtered. And the filtrate was concentrated. The residue was used for alkylation without further purification (209 mg, 100%). $^{1}$H-NMR (500 MHz, CD$_3$OD) δ ppm 7.21 (brs, 1H), 7.07 (brs, 1H), 6.11 (s, 1H), 4.46 (s, 2H), 3.95-3.89 (m, 2H), 3.39-3.34 (m, 2H), 3.08 (q, J=7.0 Hz, 2H), 3.06-2.98 (m, 3H), 2.79-2.72 (m, 1H), 2.72-2.65 (m, 2H), 2.38 (s, 3H), 2.28 (s, 3H), 2.25 (s, 3H), 1.94-1.88 (m, 2H), 1.73-1.68 (m, 2H), 1.68-1.56 (m, 4H), 0.85 (t, J=7.0 Hz, 3H); MS (ESI) [M+H]$^+$ 505.5.

N-((4,6-Dimethyl-2-oxo-1,2-dihydropyridin-3-yl)methyl)-3-(ethyl(tetrahydro-2H-pyran-4-yl)amino)-2-methyl-5-((1-methylpiperidin-4-yl)ethynyl)benzamide

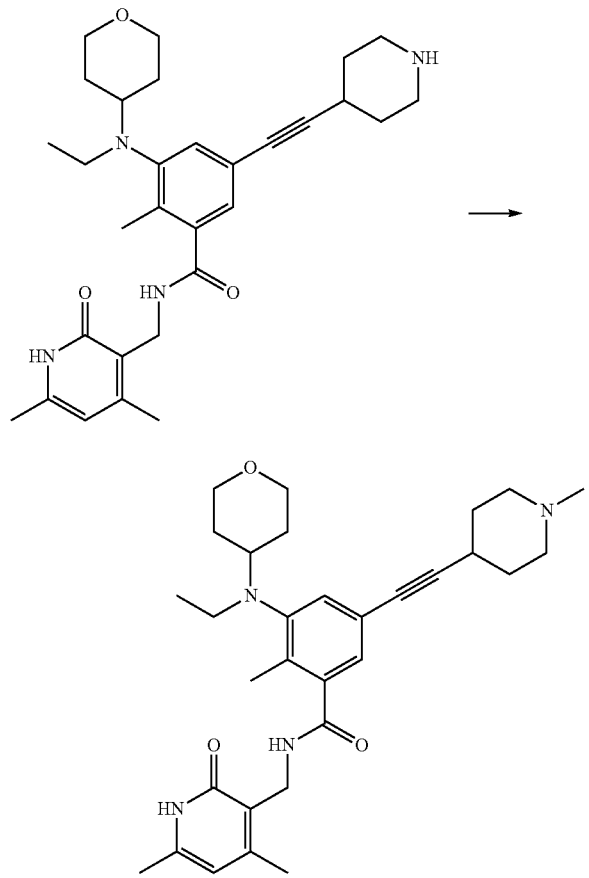

To a solution of N-((4,6-dimethyl-2-oxo-1,2-dihydropyridin-3-yl)methyl)-3-(ethyl(tetrahydro-2H-pyran-4-yl)amino)-2-methyl-5-(piperidin-4-ylethynyl)benzamide (100 mg, 0.198 mmol) in methanol (5 mL) was added 35% formaldehyde in H$_2$O (0.155 mL, 1.98 mmol) at 0° C. After stirring at 0° C. for 10 min, sodium cyanoborohydride (24.9 mg, 0.396 mmol) was added. The resulting mixture was stirred at 0° C. for 1 h. LCMS indicated that the reaction was completed. The reaction was quenched with sat. NaHCO$_3$/brine and extracted with EtAOc/Heptane. The organic layer was dried (Na$_2$SO$_4$), filtered and concentrated. The residue was purified by chromatography (10 g column, MeOH/DCM=1:9, and then MeOH/7 M NH$_3$ in MeOH/DCM=1:1: 8) to afford the titled compound (96.0 mg, 93%). $^1$H-NMR (500 MHz, CD$_3$OD) δ ppm 7.22 (brs, 1H), 7.08 (brs, 1H), 6.10 (s, 1H), 4.46 (s, 2H), 3.94-3.87 (m, 2H), 3.35-3.30 (m, 2H), 3.07 (q, J=7.0 Hz, 2H), 3.04-2.97 (m, 1H), 2.79-2.71 (m, 2H), 2.67-2.58 (m, 1H), 2.38 (s, 3H), 2.28 (s, 3H), 2.28 (s, 3H), 2.25 (s, 3H), 2.28-2.21 (m, 2H), 1.97-1.91 (m, 2H), 1.78-1.67 (m, 4H), 1.64-1.54 (m, 2H), 0.85 (t, J=7.0 Hz, 3H); MS (ESI) [M+H]$^+$ 519.4.

Example 2

Bioassay Protocol and General Methods

Protocol for Wild-Type and Mutant PRC2 Enzyme Assays

General Materials. S-adenosylmethionine (SAM), S-adenosylhomocyteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates. Peptides representative of human histone H3 residues 21-44 containing either an unmodified lysine 27 (H3K27me0) or dimethylated lysine 27 (H3K27me2) were synthesized with a C-terminal G(K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

```
H3K27me0:
                               (SEQ ID NO: 1)
ATKAARKSAPATGGVKKPHRYRPGGK(biotin)-amide H3K27me2:
                               (SEQ ID NO: 2)
ATKAARK(me2)SAPATGGVKKPHRYRPGGK(biotin)-amide
```

Chicken erythrocyte oligonucleosomes were purified from chicken blood according to established procedures.

Recombinant PRC2 Complexes. Human PRC2 complexes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates. The assays were all performed in a buffer consisting of 20 mM bicine (pH=7.6), 0.5 mM DTT, 0.005% BSG and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 2, below. The assays were stopped by the addition of non-radioactive SAM (10 μL) to a final concentration of 600 μM, which dilutes the $^3$H-SAM to a level where its incorporation into the peptide substrate is no longer detectable. 50 μL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 2

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate. The assays were performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). The final concentrations were as follows: wild-type PRC2 enzyme was 4 nM, non-radioactive SAM was 430 nM, $^3$H-SAM was 120 nM, chicken erythrocyte olignonucleosome was 120 nM, SAH in the minimum signal control wells was 1 mM and the DMSO concentration was 1%. The assay was stopped by the addition of non-radioactive SAM (10 μL) to a final concentration of 600 μM, which dilutes the $^3$H-SAM to a level where its incorporation into the chicken erythrocyte olignonucleosome substrate is no longer detectable. 50 μL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte olignonucleosome bound to the Flashplate surface, measured as disintegrations per minute (dpm) or alternatively, referred to as counts per minute (cpm).

% Inhibition Calculation $$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-parameter $IC_{50}$ fit $$Y = \text{Bottom} + \frac{(\text{Top-Bottom})}{1 + \left(\frac{x}{IC_{50}}\right)^{\text{Hill Coefficient}}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type and Y641F) are presented in Table 3 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer (5×) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10×PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA. V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 μL per well. Compound (1 μL) from 96 well source plates was added directly to V-bottom cell plate. Plates were incubated on a titer-plate shaker at 37° C., 5% CO2 for 96 hours. After four days of incubation, plates were spun at 241×g for five minutes and medium was aspirated gently from each well of cell plate without disturbing cell pellet. Pellet was resuspended in 200 μL DPBS and plates were spun again at 241×g for five minutes. The supernatant was aspirated and cold (4° C.) Extraction buffer (100 μL) was added per well. Plates were incubated at 4° C. on orbital shaker for two hours. Plates were spun at 3427×g×10 minutes. Supernatant (80 μL per well) was transferred to its respective well in 96 well V-bottom polypropylene plate. Neutralization Buffer 5× (20 μL per well) was added to V-bottom polypropylene plate containing supernatant. V-bottom polypropylene plates containing crude histone preparation (CHP) were incubated on orbital shaker×five minutes. Crude Histone Preparations were added (2 μL per well) to each respective well into duplicate 96 well ELISA plates containing 100 μL Coating Buffer (1×PBS+BSA 0.05% w/v). Plates were sealed and incubated overnight at 4° C. The following day, plates were washed three times with 300 μL, per well 1×PBST. Wells were blocked for two hours with 300 μL per well ELISA Diluent ((PBS (1×) BSA (2% w/v) and Tween20 (0.05% v/v)). Plates were washed three times with 1×PBST. For the Histone H3 detection plate, 100 μL per well were added of anti-Histone-H3 antibody (Abcam, ab1791) diluted 1:10,000 in ELISA Diluent. For H3K27 trimethylation detection plate, 100 μL per well were added of anti-H3K27me3 diluted 1:2000 in ELISA diluent. Plates were incubated for 90 minutes at room temperature. Plates were washed three times with 300 μL 1×PBST per well. For Histone H3 detection, 100 μL of HRP-conjugated anti-rabbit IgG antibody diluted to 1:6000 in ELISA diluent was added per well. For H3K27me3 detection, 100 μL of HRP conjugated anti-rabbit IgG antibody diluted to 1:4000 in ELISA diluent was added per well. Plates were incubated at room temperature for 90 minutes. Plates were washed four times with 1×PBST 300 μL per well. TMB substrate 100 μL was added per well. Histone H3 plates were incubated for five minutes at room temperature. H3K27me3 plates were incubated for 10 minutes at room temperature. The reaction was stopped with sulfuric acid 1N (100 μL per well). Absorbance for each plate was read at 450 nm.

First, the ratio for each well was determined by:

$$\left(\frac{H3K27me3\ OD450\ value}{Histone\ H3\ OD450\ value}\right)\left(\frac{H3K27me3\ OD450\ value}{Histone\ H3\ OD450\ value}\right)$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 μM. Percent inhibition was determined and $IC_{50}$ curves were generated using duplicate wells per concentration of compound. $IC_{50}$ values for this assay are presented in Table 3 below.

Percent Inhibition = 100 −

$$\left(\left(\frac{(Individual\ Test\ Sample\ Ratio) - (Background\ Avg\ Ratio)}{(Minimum\ Inhibition\ Ratio) - (Background\ Average\ Ratio)}\right)*100\right)$$

$$\left(\left(\frac{(Individual\ Test\ Sample\ Ratio) - (Background\ Avg\ Ratio)}{(Minimum\ Inhibition\ Ratio) - (Background\ Average\ Ratio)}\right)*100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 μl of assay medium. A compound source plate was prepared by performing triplicate nine-point 3-fold serial dilutions in DMSO, beginning at 10 mM (final top concentration of compound in the assay was 20 μM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity >90% for 6 days. Cell viability was measured by quantization of ATP present in the cell cultures, adding 35 μl of Cell Titer Glo® reagent to the cell plates. Luminescence was read in the SpectraMax M5. The concentration inhibiting cell viability by 50% was determined using a 4-parametric fit of the normalized dose response curves. $IC_{50}$ values for this assay are also presented in Table 3 below. The mass spectral data for these compounds are also listed in Table 3 below.

TABLE 3

| Compound# | ELISA H3K27me3 IC50 (uM) | WSU proliferation IC50 (uM) | WT EZH2 IC50 (uM) | EZH2 $IC_{50}$ peptide v2 (μM) | MS (free form) |
|---|---|---|---|---|---|
| 1 | 0.077 | 0.0230 | | <0.005 | 588.37 |
| 2 | 0.11043 | 0.38533 | | 0.01498 | 605.81 |
| 105 | 0.058-0.150 | 0.325 | <0.01 | 0.0084 | 518.3257 |

Example 3

Derivation of the Lowest Cytotoxic Concentration (LCC)

It is well established that cellular proliferation proceeds through cell division that results in a doubling of the number of cells after division, relative to the number of cells prior to division. Under a fixed set of environmental conditions (e.g., pH, ionic strength, temperature, cell density, medium content of proteins and growth factors, and the like) cells will proliferate by consecutive doubling (i.e., division) according to the following equation, provided that sufficient nutrients and other required factors are available.

$$N_t = N_0 \times 2^{\frac{t}{t_D}} \quad (A.1)$$

where $N_t$ is the cell number at a time point (t) after initiation of the observation period, $N_0$ is the cell number at the initiation of the observation period, t is the time after initiation of the observation period and $t_D$ is the time interval required for cell doubling, also referred to as the doubling time. Equation A.1 can be converted into the more convenient form of an exponential equation in base e, taking advantage of the equality, 0.693=ln(2).

$$N_t = N_0 e^{\frac{0.693 t}{t_D}} \quad (A.2)$$

The rate constant for cell proliferation ($k_p$) is inversely related to the doubling time as follows.

$$k_p = \frac{0.693}{t_D} \quad (A.3)$$

Combining equation A.2 and A.3 yields, $$N_t = N_0 e^{k_p t} \quad (A.4)$$

Thus, according to equation A.4 cell number is expected to increase exponentially with time during the early period of cell growth referred to as log-phase growth. Exponential equations like equation A.4 can be linearized by taking the natural logarithm of each side.

$$\ln(N_t) = \ln(N_0) + k_p t \quad (A.5)$$

Thus a plot of $\ln(N_t)$ as a function of time is expected to yield an ascending straight line with slope equal to $k_p$ and y-intercept equal to $\ln(N_0)$.

Changes in environmental conditions can result in a change in the rate of cellular proliferation that is quantifiable as changes in the proliferation rate constant $k_p$. Among conditions that may result in a change in proliferation rate is the introduction to the system of an antiproliferative compound at the initiation of the observation period (i.e., at t=0). When an antiproliferative compound has an immediate impact on cell proliferation, one expects that plots of $\ln(N_t)$ as a function of time will continue to be linear at all compound concentrations, with diminishing values of $k_p$ at increasing concentrations of compound.

Depending on the mechanistic basis of antiproliferative action, some compounds may not immediately effect a change in proliferation rate. Instead, there may be a period of latency before the impact of the compound is realized. In such cases a plot of $\ln(N_t)$ as a function of time will appear biphasic, and a time point at which the impact of the compound begins can be identified as the breakpoint between phases. Regardless of whether a compound's impact on proliferation is immediate or begins after a latency period, the rate constant for proliferation at each compound concentration is best defined by the slope of the $\ln(N_t)$ vs. time curve from the time point at which compound impact begins to the end of the observation period of the experiment.

A compound applied to growing cells may affect the observed proliferation in one of two general ways: by inhibiting further cell division (cytostasis) or by cell killing (cytotoxicity). If a compound is cytostatic, increasing concentration of compound will reduce the value of $k_p$ until there is no further cell division. At this point, the rate of cell growth, and therefore the value of $k_p$, will be zero. If, on the other hand, the compound is cytotoxic, then the value of $k_p$ will be composed of two rate constants: a rate constant for continued cell growth in the presence of the compound ($k_g$) and a rate constant for cell killing by the compound ($k_d$). The overall rate constant for proliferation at a fixed concentration of compound will thus be the difference between the absolute values of these opposing rate constants.

$$k_p = |k_g| - |k_d| \quad (A.6)$$

At compound concentrations for which the rate of cell growth exceeds that of cell killing, the value of $k_p$ will have a positive value (i.e., $k_p > 0$). At compound concentrations for which the rate of cell growth is less than that for cell killing, the value of $k_p$ will have a negative value (i.e., $k_p < 0$) and the cell number will decrease with time, indicative of robust cytotoxicity. When $k_g$ exactly matches $k_d$ then the overall proliferation rate constant, $k_p$, will have a value of zero. We can thus define the lowest cytotoxic concentration (LCC) as that concentration of compound that results in a value of $k_p$ equal to zero, because any concentration greater than this will result in clearly observable cytotoxicity. Nota bene: at concentrations below the LCC there is likely to be cell killing occurring, but at a rate that is less than that of residual cell proliferation. The treatment here is not intended to define the biological details of compound action. Rather, the goal here is to merely define a practical parameter with which to objectively quantify the concentration of compound at which the rate of cell killing exceeds new cell growth. Indeed, the LCC represents a breakpoint or critical concentration above which frank cytotoxicity is observed, rather than a cytotoxic concentration per se. In this regard, the LCC can be viewed similar to other physical breakpoint metrics, such as the critical micelle concentration (CMC) used to define the concentration of lipid, detergent or other surfactant species above which all molecules incorporate into micellar structures.

Traditionally, the impact of antiproliferative compounds on cell growth has been most commonly quantified by the $IC_{50}$ value, which is defined as that concentration of compound that reduces the rate of cell proliferation to one half that observed in the absence of compound (i.e., for the vehicle or solvent control sample). The $IC_{50}$, however, does not allow the investigator to differentiate between cytostatic and cytotoxic compounds. The LCC, in contrast, readily allows one to make such a differentiation and to further quantify the concentration at which the transition to robust cytotoxic behavior occurs.

If one limits the observation time window to between the start of impact and the end of the experiment, then the data will generally fit well to a linear equation when plotted as $\ln(N_t)$ as a function of time (vide supra). From fits of this type, the value of $k_p$ can be determined at each concentration of compound tested. A replot of the value of $k_p$ as a function of compound concentration ([I]) will have the form of a descending isotherm, with a maximum value at [I]=0 of $k_{max}$ (defined by the vehicle or solvent control sample) and a minimum value at infinite compound concentration of $k_{min}$.

$$k_p = \frac{(k_{max} - k_{min})}{1 + \frac{[I]}{I_{mid}}} + k_{min} \quad (A.7)$$

where $I_{mid}$ is the concentration of compound yielding a value of $k_p$ that is midway between the values of $k_{max}$ and $k_{min}$ (note that the value of $I_{mid}$ is not the same as the $IC_{50}$, except in the case of a complete and purely cytostatic compound). Thus, fitting the replot data to equation A.7 provides estimates of $k_{max}$, $k_{min}$ and $I_{mid}$. If a compound is cytostatic (as defined here), the value of $k_{min}$ cannot be less than zero. For cytotoxic compounds, $k_{min}$ will be less than zero and the absolute value of $k_{min}$ will relate directly to the effectiveness of the compound in killing cells.

The fitted values derived from equation A.7 can also be used to determine the value of the LCC. By definition, when [I]=LCC, $k_p$=0. Thus, under these conditions equation A.7 becomes.

$$0 = \frac{(k_{max} - k_{min})}{1 + \frac{LCC}{I_{mid}}} + k_{min} \quad (A.8)$$

Algebraic rearrangement of equation A.8 yields an equation for the LCC.

$$LCC = I_{mid}\left[\left(\frac{k_{max} - k_{min}}{-k_{min}}\right) - 1\right] \quad (A.9)$$

This analysis is simple to implement with nonlinear curve fitting software and may be applied during cellular assays of compound activity throughout the drug discovery and development process. In this manner, the LCC may provide a valuable metric for the assessment of compound SAR (structure-activity relationship).

Example 4

In Vivo Assays

Mice

Female Fox Chase SCID® Mice (CB 17/Icr-Prkdc$_{scid}$/IcrIcoCrl, Charles River Laboratories) or athymic nude mice (Crl:NU(Ncr)-Foxnl$_{nu}$, Charles River Laboratories) were 8 weeks old and had a body-weight (BW) range of 16.0-21.1 g on Day 1 of the study. The animals were fed ad libitum water (reverse osmosis 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity. All procedures complied with the recommendations of the *Guide for Care and Use of Laboratory Animals* with respect to restraint, husbandry, surgical procedures, feed and fluid regulation, and veterinary care.

Tumor Cell Culture

Human lymphoma cell lines line were obtained from different sources (ATCC, DSMZ), e.g., Karpas-422 obtained from DSMZ. The cell lines were maintained as suspension cultures in RPMI-1640 medium containing 100 units/mL penicillin G sodium salt, 100 g/mL streptomycin, 1% HEPES, and 1% L-Glutamine. The medium was supplemented with 20% fetal bovine serum. The cells were cultured in tissue culture flasks in a humidified incubator at 37° C., in an atmosphere of 5% $CO_2$ and 95% air.

In Vivo Tumor Implantation

Human lymphoma cell lines, e.g., Karpas-422 cells, were harvested during mid-log phase growth, and re-suspended in RPMI-1640 base media and 50% Matrigel™ (BD Biosciences) (RPMI:Matrigel=1:1). Each mouse received 1×10$^7$ cells (0.2 mL cell suspension) subcutaneously in the right flank. Tumors were calipered in two dimensions to monitor growth as the mean volume approached the desired 80-120 mm$^3$ range. Tumor size, in mm$^3$, was calculated from:

$$\text{Tumor volume} = \frac{w^2 \times l}{2}$$

where w=width and l=length, in mm, of the tumor. Tumor weight can be estimated with the assumption that 1 mg is equivalent to 1 mm$^3$ of tumor volume. After 10-30 days mice with 145-150 mm$^3$ tumors were sorted into treatment groups with mean tumor volume of 147 mm$^3$.

Test Articles

Test compounds were stored at room temperature and protected from light. On each treatment day, fresh compound formulations were prepared by suspending the powders in 0.5% sodium carboxymethylcellulose (NaCMC) and 0.1% Tween® 80 in deionized water. The vehicle, 0.5% NaCMC and 0.1% Tween® 80 in deionized water, was used to treat the control groups at the same schedules. Formulations were stored away from light at 4° C. prior to administration. Unless otherwise specified, compounds referred to and tested in this experiment were in their specific salt forms mentioned in this paragraph.

Treatment Plan

Mice were treated at compound doses ranging from 62.5-500 mg/kg on a BID (2 times a day every 12 h) schedule for various amounts of days by oral gavage. Each dose was delivered in a volume of 0.2 mL/20 g mouse (10 mL/kg), and adjusted for the last recorded weight of individual animals. The maximal treatment length was 28 days.

Median Tumor Volume (MTV) and Tumor Growth Inhibition (TGI) Analysis

Treatment efficacy was determined on the last treatment day. MTV(n), the median tumor volume for the number of animals, n, evaluable on the last day, was determined for each group. Percent tumor growth inhibition (% TGI) can be defined several ways. First, the difference between the MTV(n) of the designated control group and the MTV(n) of the drug-treated group is expressed as a percentage of the MTV(n) of the control group:

$$\% \, TGI = \left(\frac{MTV(n)_{control} - MTV(n)_{treated}}{MTV(n)_{control}}\right) \times 100$$

Another way of calculating % TGI is taking the change of the tumor size from day 1 to day n into account with n being the last treatment day.

$$\% \, TGI = \left(\frac{\Delta MTV_{control} - \Delta MTV_{treated}}{\Delta MTV_{control}}\right) \times 100$$

$$\Delta MTV_{control} = MTV(n)_{control} - MTV(1)_{control}$$

$$\Delta MTV_{treated} = MTV(n)_{treated} - MTV(1)_{treated}$$

Toxicity

Animals were weighed daily on Days 1-5, and then twice weekly until the completion of the study. The mice were examined frequently for overt signs of any adverse, treatment related side effects, which were documented. Acceptable toxicity for the maximum tolerated dose (MTD) was defined as a group mean BW loss of less than 20% during the test, and not more than 10% mortality due to TR deaths. A death is to be classified as TR if it is attributable to treatment side effects as evidenced by clinical signs and/or necropsy, or due to unknown causes during the dosing period. A death is to be classified as NTR if there is evidence that the death is unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On days 7 or 28 during the studies mice were sampled in a pre-specified fashion to assess target inhibition in tumors. Tumors were harvested from specified mice under RNAse free conditions and bisected. Frozen tumor tissue from each animal was snap frozen in liquid $N_2$ and pulverized with a mortar and pestle.

Statistical and Graphical Analyses

All statistical and graphical analyses were performed with Prism 3.03 (GraphPad) for Windows. To test statistical significance between the control and treated groups over the whole treatment time coursed a repeated measures ANOVA test followed by Dunnets multiple comparison post test or a 2 way ANOVA test were employed. Prism reports results as non-significant (ns) at P>0.05, significant (symbolized by "*") at 0.01<P<0.05, very significant ("") at 0.001<P<0.01 and extremely significant ("*") at P<0.001.

Histone Extraction

For isolation of histones, 60-90 mg tumor tissue was homogenized in 1.5 ml nuclear extraction buffer (10 mM Tris-HCl, 10 mM MgCl2, 25 mM KCl, 1% Triton X-100, 8.6% Sucrose, plus a Roche protease inhibitor tablet 1836145) and incubated on ice for 5 minutes. Nuclei were collected by centrifugation at 600 g for 5 minutes at 4° C. and washed once in PBS. Supernatant was removed and histones extracted for one hour, with vortexing every 15 minutes, with 0.4 N cold sulfuric acid. Extracts were clarified by centrifugation at 10000 g for 10 minutes at 4° C. and transferred to a fresh microcentrifuge tube containing 10× volume of ice cold acetone. Histones were precipitated at −20° C. for 2 hours-overnight, pelleted by centrifugation at 10000 g for 10 minutes, and resuspended in water.

ELISA

Histones were prepared in equivalent concentrations in coating buffer (PBS+0.05% BSA) yielding 0.5 ng/uL of sample, and 100 uL of sample or standard was added in duplicate to 2 96-well ELISA plates (Thermo Labsystems, Immulon 4HBX #3885). The plates were sealed and incubated overnight at 4° C. The following day, plates were washed 3× with 300 uL/well PBST (PBS+0.05% Tween 20; 10×PBST, KPL #51-14-02) on a Bio Tek plate washer. Plates were blocked with 300 uL/well of diluent (PBS+2% BSA+ 0.05% Tween 20), incubated at RT for 2 hours, and washed 3× with PBST. All antibodies were diluted in diluent. 100 uL/well of anti-H3K27me3 (CST #9733, 50% glycerol stock 1:1,000) or anti-total H3 (Abcam ab1791, 50% glycerol 1:10,000) was added to each plate. Plates were incubated for 90 min at RT and washed 3× with PBST. 100 uL/well of anti-Rb-IgG-HRP (Cell Signaling Technology, 7074) was added 1:2,000 to the H3K27Me3 plate and 1:6,000 to the H3 plate and incubated for 90 min at RT. Plates were washed 4× with PBST. For detection, 100 uL/well of TMB substrate (BioFx Laboratories, #TMBS) was added and plates incubated in the dark at RT for 5 min. Reaction was stopped with 100 uL/well 1N $H_2SO_4$. Absorbance at 450 nm was read on SpectraMax M5 Microplate reader.

7 Day PD Study

In order to test whether a compound can modulate the H3K27me3 histone mark in tumors in vivo, Karpas-422 xenograft tumor bearing mice were treated with the compound at 62.5, 83.3, 125, 166.7, 250, 333.3, or 500 mg/kg BID or vehicle (BID schedule) for 7 days. There were 5 animals per group. Animals were euthanized 3 h after the last dose and tumor was preserved in a frozen state as described above. Following histone extraction the samples were applied to ELISA assays using antibodies directed against the trimethylated state of histone H3K27 (H3K27me3) or total histone H3. Based on these data the ratio of globally methylated to total H3K27 was calculated. The mean global methylation ratios for all groups as measured by ELISA indicate target inhibition range compared to vehicle. The design for this experiment is shown in Table 4A.

TABLE 4A

Dosing Scheme

| Group | N | Treatment | Dose (mg/kg) | Dosing volume | Dosing Route | Schedule |
|---|---|---|---|---|---|---|
| 1 | 5 | Vehicle | — | 10 μl/g. | p.o. | BID × 7 |
| 2 | 5 | Compound 1 | 62.5 | 10 μl/g | p.o. | BID × 7 |
| 3 | 5 | Compound 1 | 83.3 | 10 μl/g. | p.o. | BID × 7 |
| 4 | 5 | Compound 1 | 125 | 10 μl/g | p.o. | BID × 7 |
| 5 | 5 | Compound 1 | 166.7 | 10 μl/g | p.o. | BID × 7 |
| 6 | 5 | Compound 1 | 250 | 10 μl/g | p.o. | BID × 7 |
| 7 | 5 | Compound 1 | 333.3 | 10 μl/g. | p.o. | BID × 7 |
| 8 | 5 | Compound 1 | 500 | 10 μl/g | p.o. | BID × 7 |
| 9 | 5 | Compound A* | 125 | 10 μl/g. | p.o. | BID × 7 |
| 10 | 5 | Compound A | 250 | 10 μl/g. | p.o. | BID × 7 |

*Compound A is N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide.

Example 5

Efficacy Study with Increasing Doses in Karpas-422 Xenograft Model

In order to test whether a compound could induce an anti-tumor effect in vivo, Karpas-422 xenograft tumor bearing mice were treated with a compound at, e.g., 62.5, 125, 250, or 500 mg/kg BID for 28 days. There were 10 mice per group for the efficacy arm of the experiment. The tumor growth over the treatment course of 28 days for vehicle and test compound treated groups was measured.

Histones were extracted from tumors collected at the end of the study on day 28 for the efficacy cohort (3 h after the last dose for both cohorts). The H3K27me3 methyl mark was assessed for modulation with treatment in a dose dependent matter.

The design for this experiment is shown in Table 4B.

TABLE 4B

Dosing Scheme

| Group | N | Treatment | Dose (mg/kg) | Dosing volume | Dosing Route | Schedule |
|---|---|---|---|---|---|---|
| 1 | 10 | Vehicle | — | 10 μl/g. | p.o. | BID × 28 |
| 2 | 10 | Compound 1 | 62.5 | 10 μl/g | p.o. | BID × 28 |
| 3 | 10 | Compound 1 | 125 | 10 μl/g. | p.o. | BID × 28 |
| 4 | 10 | Compound 1 | 250 | 10 μl/g. | p.o. | BID × 28 |
| 5 | 10 | Compound 1 | 500 | 10 μl/g. | p.o. | BID × 28 |
| 6 | 10 | Compound A* | 250 | 10 μl/g. | p.o. | BID × 28 |

*Compound A is N-((4,6-dimethyl-2-oxo-1,2-dihydropyridin-3-yl)methyl)-5-(ethyl(tetranydro-2H-pyran-4-yl)amino)-4-methyl-4'-(morpholinomethyl)-[1,1'-biphenyl]-3-carboxamide.

TV was calculated from caliper measurements by the formula for the volume of a prolate ellipsoid $(L \times W^2)/2$ where L and W are the respective orthogonal length and width measurements (mm).

Data were expressed as the mean±standard deviation (SD). The differences in TV between the vehicle-treated and compound-treated groups were analyzed by a repeated measures analysis of variance (ANOVA) followed by the Dunnett-type multiple comparison test. A value of P<0.05 (two sided) is considered statistically significant. Statistical analyses were performed using the Prism 5 software package version 5.04 (GraphPad Software, Inc., CA, USA).

Figure 1:
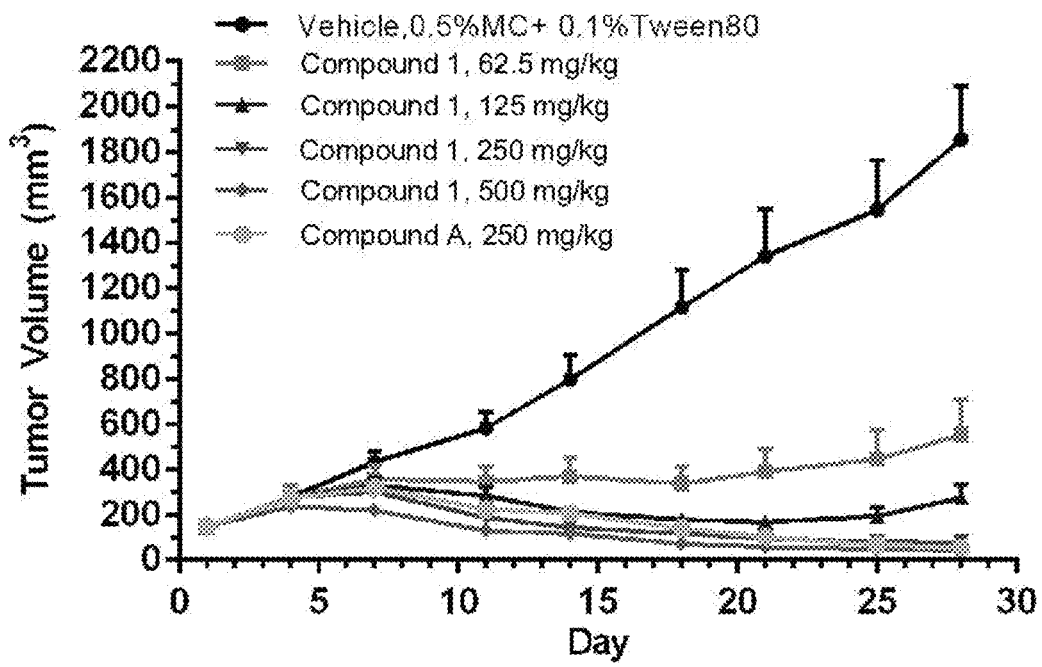
FIG. 1 is a diagram showing antitumor effects of orally administered Compound 1 or Compound A against a lymphoma KARPAS-422 xenograft in mice. Data represent the mean±SD (n=10).
Figure 2:
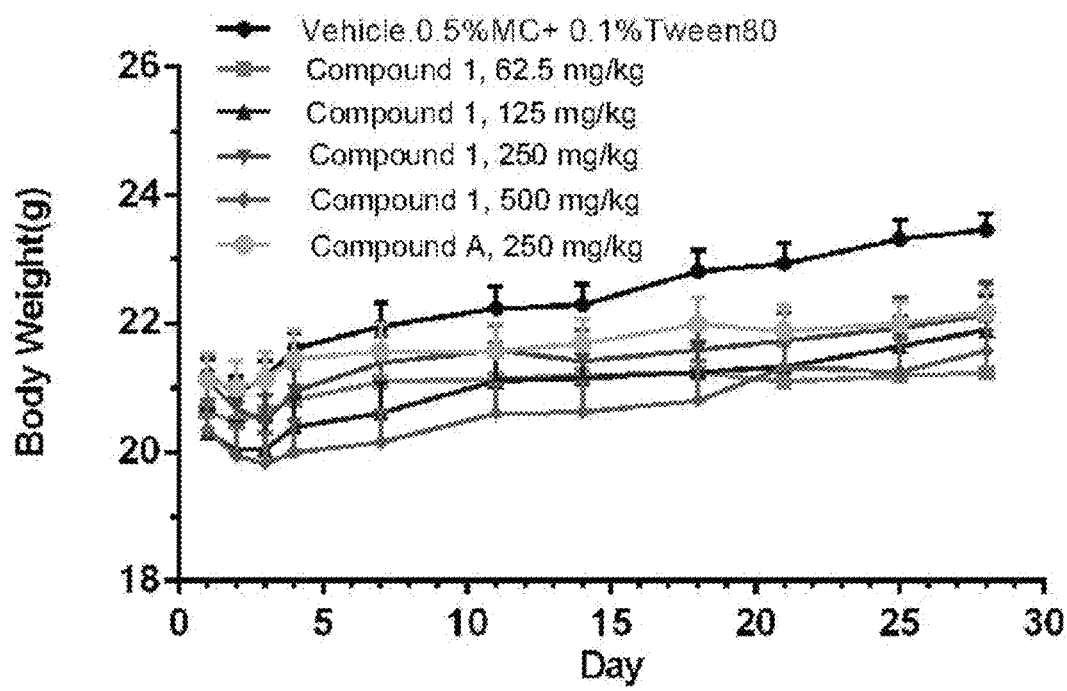
FIG. 2 is a diagram showing effect of Compound 1 or Compound A on mouse body weight. Data represent the mean±SD (n=10).

The above studies showed that both Compound 1 and Compound A exhibited tumor stasis and regression in Karpas-422 xenograft model and were well tolerated. See, e.g., FIGS. 1 and 2. Further, the pharmacokinetic and pharmacodynamic properties of Compound 1 or Compound A from the above studies are illustrated in FIGS. 3-8. FIG. 3 is a diagram showing concentration of Compound 1 in tumor at day 7 or day 28 post treatment or concentration of Compound A in tumor at day 7 post treatment. In this figure, "A" though "G" denote 7 days post administration of Compound 1 at dosages of 62.5, 83.3, 125, 166.7, 250, 333.3, and 500 mg/kg, respectively; "H" and "I" denote 7 days post administration of Compound A at dosages of 125 and 250 mg/kg, respectively; and "J" through "L" denote 28 days post administration of Compound 1 at dosages of 62.5, 125 and 250 mg/kg, respectively. Note: for samples at day 28, tumors were too small for analysis from the group treated with 250 mg/kg Compound A and the group treated with 500 mg/kg Compound 1; only 1 out of 10 and 5 out of 10 were large enough for analysis from groups treated with 250 mg/kg Compound 1 and 125 mg/kg Compound 1, respectively. FIG. 4 is a diagram showing concentration of Compound 1 or Compound A in plasma at day 7 or day 28 post treatment. The top dashed line indicates the plasma protein binding (PPB) corrected LCC of Compound A and the bottom dashed line indicates PPB corrected LCC of Compound 1. FIG. 5 is a diagram showing global H3K27me3 methylation in KARPAS-422 tumors from mice treated with Compound 1 or Compound A for 7 days. In this figure, "A" denotes vehicle treatment; "B" though "H" denote treatment with Compound 1 at dosages of 62.5, 83.3, 125, 166.7, 250, 333.3, and 500 mg/kg, respectively; and "I" and "J" denote treatment with Compound A at dosages of 125 and 250 mg/kg, respectively. FIG. 6 is a diagram showing global H3K27me3 methylation in KARPAS-422 tumors from mice treated with Compound 1 for 28 days. FIG. 7 is a diagram showing global H3K27me3 methylation in bone marrow from KARPAS-422 xenograft tumor bearing mice treated with Compound 1 or Compound A for 7 days. In this figure, "A" denotes vehicle treatment; "B" though "H" denote treatment with Compound 1 at dosages of 62.5, 83.3, 125, 166.7, 250, 333.3, and 500 mg/kg, respectively; and "I" and "J" denote treatment with Compound A at dosages of 125 and 250 mg/kg, respectively. FIG. 8 is a diagram showing global H3K27me3 methylation in bone marrow from KARPAS-422 xenograft tumor bearing mice treated with Compound 1 for 28 days. In this figure, "A" denotes vehicle treatment; "B" though "E" denote treatment with Compound 1 at dosages of 62.5, 125, 250, and 500 mg/kg, respectively; and "F" denotes treatment with Compound A at a dosage of 250 mg/kg.

In Examples 6-8 below, experiments and analyses were conducted with methods and techniques similar to those described in e.g., J. Lin, *Pharmaceutical Research*, 2006, 23(6):1089-1116; L. Di et al., *Comb Chem High Throughput Screen*. 2008, 11(6):469-76; M. Fonsi et al., *Journal of Biomolecular Screening*, 2008, 13:862; E. Sjögren et al., *Drug Metab. Dispos*. 2012, 40:2273-2279; T. D. Bjornsson, et al., *Drug Metab Dispos*, 2003, 31(7):815-832; J. B. Houston and K. E. Kenworthy, *Drug Metab Dispos*, 2000, 28(3):246-254; and S. W. Grimm et al., *Drug Metab Dispos*, 2009, 37(7):1355-1370, the contents of each of which are hereby incorporated by reference in their entireties.

Example 6

Assessment of Metabolic Stability in Liver Microsomes

The metabolic stability of Compounds 1, 2, and 105, were evaluated in liver microsomes from five species, including mice, rats, dogs, monkeys, and humans.

Methods: The incubations were conducted in 96-well plates containing 250 µL total volume consisting of 100 mmol/L potassium phosphate buffer (pH 7.4), 1 mg/mL liver microsomes, test compound (i.e., Compounds 1, 2, or 105) at 8 concentrations, and 2 mg/mL NADPH. The concentrations of the compounds used for incubation ranged from 45.7 nM to 100 µM. The addition of NADPH was used to start the reaction, and the incubations were done in a shaking water bath at 37° C. for up to 60 minutes. The reactions were terminated by adding an equal volume of stop solution containing Internal Standard (IS). The samples were then spun in a refrigerated centrifuge at 3000 RPM for a minimum of 5 minutes prior to analysis. The amount of depletion in the incubation mixes for the test compound, as determined by using LC/TOFMS, was used to estimate intrinsic clearance values with liver microsomes. The LC/TOFMS systems were composed of a Shimadzu SIL-HTC autosampler (Kyoto, Japan), two pumps LC-20AD; Shimadzu Corp.), and a column oven (CTO-20AC; Shimadzu Corp.) with a time-of-flight mass spectrometer (AB SCIEX Qstar Elite, AB Sciex, Foster City, Calif.). Peak areas of the test compound and IS for assay were integrated by Analyst QS (version 2.0, Applied Biosystems, Foster City, Calif.). Collision activated dissociation (CAD) with nitrogen was used to generate product ions. The optimized instrumental conditions were under positive ionization mode.

The LC/MS/MS quantification was based on the ratios of peak areas of the test compound to that of the IS. Peak area calculation and integration of Compounds 1, 2, or 105 and IS utilized Analyst QS 2.0 (AB Sciex, Foster City, Calif.). Calculations were done using Excel (Office 2010, Microsoft Corp., Redmond, Wash.) and GraphPad Prism v. 5.02 (GraphPad Software Inc., La Jolla, Calif.). Data was analyzed and reported based on appropriate SOPs, such as those described in J. Lin, *Pharmaceutical Research*, 2006, 23(6): 1089-1116; and Di L et al., *Comb Chem High Throughput Screen*. 2008 11(6):469-76.

The depletion of the test compound used for $K_m$ and $V_{max}$ values with liver microsomes was calculated by plotting against time to determine the rate of depletion. The rates of depletion were then plotted using an appropriate kinetic model. The data were calculated based on the following equations:

$$\text{Michaelis-Menten: } Cl_{int}(\mu L/\text{min/mg of liver microsomes}) = V_{max}/K_m$$

$$\text{Hill: } Cl_{int}(4/\text{min/mg of liver microsomes}) = Cl_{max} = V_{max}/K_s \cdot (n-1)/(n(n-1)^{1/n})$$

$$Cl_{int}(\mu L/\text{min/g liver}) = Cl_{int}(\mu L/\text{min/mg microsomes}) \cdot \text{Scaling Factor or } Cl_{int}(\mu L/\text{min}/10^6 \text{ cells}) \cdot \text{Scaling Factor.}$$

The results are provided in Table 5 below.

TABLE 5

| | Estimated Intrinsic Clearance (mL/min/kg) | | | | |
|---|---|---|---|---|---|
| | Mouse | Rat | Dog | Cyno | Human |
| Compound 1 | 15.4 | 14.8 | 8.1 | 58.6 | 10.5 |
| Compound 105 | 54.7 | 47.5 | 64.2 | 74.8 | 42.1 |
| Compound 2 | 17.6 | 14.8 | 34.3 | 32.8 | 8.8 |

All of the three tested compound, i.e., Compounds 1, 2, and 105 exhibited low metabolic clearance in human liver microsomes (HLM). Species difference in metabolic clearance was also observed. Cynomolgus monkeys generally showed higher clearance than other species.

Example 7

Assessment of CYP Induction

The induction of each of Compounds 1, 2, and 105 was evaluated in cryopreserved human hepatocytes from a single donor.

Methods: The hepatocytes were obtained from BD Biosciences (Woburn, Mass.), and the appropriate media and DAPI nuclear stain were purchased from Life Technologies (Durham, N.C.). Dulbecco's modified Eagle's Medium (DMEM), Dulbecco's phosphate buffered saline (DPBS), 100×MEM non-essential amino acids, 100× penicillin/streptomycin/glutamine solution, 2× trypan blue were purchased from Mediatech (Manassas, Va.). Fetal bovine serum (FBS) was acquired from Tissue Culture Biologicals (Tulare, Calif.). The 24-well collagen coated plates for mRNA analysis were acquired from BD Biosciences (San Jose, Calif.). Predesigned probes and primers were used in two triplex assays to assess change in mRNA. The positive controls were β-naphthoflavone for CYP1A (1 and 10 μmol/L), phenobarbital for CYP2B6 (100 μmol and 1 mmol/L), and rifampicin for CYP2C9 and CYP3A (1 and 10 μmol/L). DMSO was used as the vehicle (negative) control. CYP form specific assays were performed after the treatment period, and cells were counted to determine viability.

The cryopreserved hepatocytes were thawed in a 37° C. water bath and plated according to vendor instructions. One tube of hepatocytes was added to a 50 mL conical tube containing Life Technologies cryopreserved hepatocyte recovery medium (CHRM). The cells were spun in a Beckman centrifuge with a GH 3.8 rotor at 800 RPM for 10 minutes. The supernatant was removed and the cells were resuspended in plating media for counting. After counting, the cells were resuspended at 0.75 million viable cells/mL. The suspension (0.5 mL/well) was added into a 24-well collagen coated plate, or, after the addition of 60 μL of DMEM containing 10% FBS, penicillin/streptomycin/glutamine, and MEM non-essential amino acids, 80 μL of the suspension was added to each well of a 96-well collagen coated plate. After swirling and rocking to provide better plate coverage, the cells were placed in a tissue culture incubator at 5% $CO_2$ and 37° C. and allowed to attach overnight. The cells were then treated using CellzDirect hepatocyte maintenance media. The cells were exposed to Compound 1, 2, or 105 (1 or 10 μmol/L) or vehicle for 48 hours. During the treatment, the maintenance media and test compounds were replenished every 24 hours.

After completion of the incubation, the cells were washed with DPBS. After washing with DPBS, the cells were fixed using 3.7% p-formaldehyde in DPBS for one hour. The formaldehyde was removed and 0.6 μmol/L DAPI in DPBS was added. The cells were stained by DAPI for 20 minutes and then washed three times with DPBS. Cells were counted using an ArrayScan II (Cellomics, Pittsburgh, Pa.) with a 5× objective lens. Fraction of hepatocytes remaining was calculated using the number of cells found at a treatment condition divided by cells found with the vehicle control.

After treatment, cells were lysed using buffer RLT from the Qiagen RNeasy kit. The mRNA was isolated using the RNeasy kit with DNase treatment using manufacturer's protocols. The mRNA concentration was measured via a Nanodrop ND-1000 (Wilmington, Del.). The mRNA concentration was normalized for every sample within a donor. The reverse transcription was performed with a Superscript VILO cDNA synthesis kit from Life Technologies following manufacturer's directions. After cDNA synthesis, quantitative real time PCR was performed using a 7500 Fast Real Time PCR system from Applied Biosystems, a wholly owned subsidiary of Life Technologies. The reaction components for real time PCR consisted of: 10 μL of Taqman Fast Advanced Master Mix (Life Technologies), 2 μL cDNA, 5 μL nuclease free water (Life Technologies), 1 μL of primer limited FAM labeled assay HS00984230_m1 for β-2 microglobulin, 1 μL of primer limited VIC labeled assay HS00167927_m1 for CYP1A2 or HS04183483_g1 for CYP2B6, and 1 μL of primer limited NED labeled assay HS04260376_m1 for CYP2C9 or HS00604506_m1 for CYP3A4. Calculations of fold difference as compared to vehicle control were done by 7500 Software version 2.0.5 (Life Technologies) using the $\Delta\Delta C_t$ method. Calculations of $E_{max}$ and $EC_{50}$ were done using GraphPad Prism.

TABLE 6

| | | CYP1A | | CYP2B6 | | CYP2C9 | | CYP3A | | |
|---|---|---|---|---|---|---|---|---|---|---|
| Compound | Concentration (μM) | Fold Induction | % Positive Control | Fold Induction | % Positive Control | Fold Induction | % Positive Control | Fold Induction | % Positive Control | % Cell Remaining vs. Control |
| 1 | 1 | 1.04 | 2.8 | 0.98 | 18.0 | 1.04 | 43.5 | 1.04 | 13.9 | 107.44 |
| | 10 | 1.14 | 3.0 | 1.43 | 26.3 | 1.26 | 52.6 | 0.99 | 13.3 | 99.00 |
| 2 | 1 | 0.73 | NA | 0.61 | NA | 0.57 | NA | 0.59 | NA | 124.70 |
| | 10 | 0.83 | NA | 0.64 | NA | 0.73 | NA | 0.73 | NA | 120.90 |
| 105 | 1 | 1.14 | 3.0 | 1.39 | 25.5 | 1.20 | 50.4 | 1.35 | 18.1 | 103.19 |
| | 10 | 1.65 | 4.4 | 2.84 | 52.2 | 1.82 | 76.3 | 2.52 | 33.8 | 97.49 |

As shown in Table 6 above, Compound 1 exhibited no significant induction (except potentially CYP2C9); Compound 2 exhibited no induction (with slightly lower activity); and Compound 105 exhibited induction of CYP2B6, CYP2C9, and CYP3A. No significant loss of cell viability was observed.

Example 8

Assessment of CYP Inhibition

The potential inhibition of enzyme activities of human cytochromes P450 (CYP) of Compound 1, 2, or 105 was evaluated using pooled human liver microsomes.

Methods: The competitive inhibition potential of Compounds 1, 2, and 105 was determined by assessing at multiple concentrations on probe CYP reactions near their respective $K_m$ values to create $IC_{50}$ curves in human liver microsomes (HLM). The time-dependent inactivation (TDI) potential was also assessed for CYP3A4/5 by evaluating $K_I$ and $k_{inact}$ values when appropriate.

A suspension containing PB, HLM, CYP-selective probe substrate, and the inhibitor being tested was added to a 96-well plate. The plates were preincubated in a 37° C. water bath for approximately 2 minutes. The reaction was initiated by the addition of NADPH to each well of the 96-well plate. The final concentrations for PB, HLM, and NADPH were 100 mmol/L (pH 7.4), 0.1 mg/mL, and 2.3 mmol/L, respectively. The CYP probe substrates and CYP inhibitors used as positive controls and their respective concentrations are listed below. The final MeOH concentration used in each incubation did not exceed 0.8%.

After the appropriate incubation time, an equal volume of the quench solution containing IS was added to the appropriate wells. Standard and quality control (QC) samples were prepared using similar components as the test samples. The blank was prepared with a similar quench solution as the other samples but did not include IS. The plates were spun for 5 minutes in a bench-top centrifuge at 3000 rpm. The samples were analyzed by LC/MS/MS. The incubation condition and the positive controls are listed in Table 7 below.

For assessing the TDI, the primary incubation, a suspension containing PB, HLM, and the inhibitor stocks was added to a 96-well plate. The plates were preincubated in a 37° C. water bath for approximately 2 minutes. The reaction was initiated by the addition of NADPH to each well of the 96-well plate and carried out for 0, 5, 10, 15, 20, and 30 minutes. For the no NADPH controls, PB solution was substituted for NADPH stock solution. The final concentrations for PB, HLM, and NADPH were 100 mmol/L (pH 7.4), 0.2 mg/mL, and 2.3 mmol/L, respectively. At the respective times, 12.5 μL of primary incubation suspension was diluted 20-fold into pre-incubated secondary incubation mixture containing CYP-selective probe substrates in order to assess residual activity. The probe substrates used was testosterone (250 μmol/L) and the positive control was troleandomycin.

The HPLC system used was a Shimadzu HPLC system (Kyoto, Japan) consisting of a SIL-HTC autosampler, a DGU-14A degasser, three LC-10ADvp pumps, and a CTO-10ACvp column oven. The samples were analyzed on an API4000QTrap (AB Sciex, Foster City, Calif.) triple quadrupole mass spectrometer using turbo spray ionization under positive ion mode.

Peak area calculation and integration of all monitored metabolites and IS were processed by Analyst 1.6 (AB Sciex, Foster City, Calif.). Quantitation was achieved with the use of calibration curves constructed by plotting the peak area ratio of metabolite to IS against concentrations of calibration standards, and was generated by quadratic regression with a $1/x^2$ weighting (y=a $x^2$+b x+c). Percent inhibition calculations utilized Excel (Office 2010, Microsoft Corp., Redmond, Wash.), and were plotted using GraphPad Prism (Version 5.02, GraphPad Software, Inc., LaJolla, Calif.) based on the assumption of one binding site. Nominal concentrations of test compounds and the positive controls were log transformed in GraphPad Prism. Using the plots of remaining CYP3A4/5 activity versus preincubation time, rate of CYP activity loss (λ) was estimated by nonlinear regression. The parameters, $k_{inact}$ and $K_I$, were subsequently estimated by fitting to the following equation:

$$\lambda = k_{inact} \times \frac{[I]}{K_I + [I]}$$

where [I] is the initial concentration of Compound 1, 2, or 105.

TABLE 7

| CYP Tested | CYP Probe Substrate | Sub. Conc. (μmol/L) | CYP Inhibitor (Positive Control) | Max. Inhib. Conc (μmol/L) | Incub. Time (min) | Internal Standard (LC/MS/MS) |
|---|---|---|---|---|---|---|
| CYP1A2 | Phenacetin | 40 | Furafylline | 20 | 10 | $^{13}C_2$, $^{15}N$-acetaminophen |
| CYP2B6 | Bupropion | 140 | Ticlopidine | 5 | 10 | $^2H_6$-hydroxybupropion |
| CYP2C8 | Amodiaquine | 10 | Montelukast | 12 | 10 | $^2H_3$-desethylamodiaquine |
| CYP2C9 | Tolbutamide | 100 | Sulfaphenazole | 20 | 10 | $^2H_9$-hydroxytolbutamide |
| CYP2C19 | (S)-Mephenytoin | 30 | (S)-Benzylnirvanol | 8 | 10 | $^2H_3$-4'-hydroxymephenytoin |
| CYP2D6 | (±)-Bufuralol | 20 | Quinidine | 2 | 5 | $^2H_9$-1'-hydroxybufuralol |
| CYP3A4/5 | Midazolam Testosterone | 3 70 | Ketoconazole | 1 | 5 | $^{13}C_3$-1'-hydroxymidazolam (R)-propranolol |

TABLE 8

| | Reversible inhibition | | | | | | |
|---|---|---|---|---|---|---|---|
| | $IC_{50}$ (μM) | | | | | | |
| Compound | CYP1A | CYP2C8 | CYP2C9 | CYP2C19 | CYP2D6 | CYP3A4/5 Midazolam | CYP3A4/5 Testosterone |
| 1 | >100 | >100 | >100 | 89.57 | 22.94 | 40.46 | >100 |
| 2 | >100 | >100 | >100 | >100 | >100 | >100 | >100 |
| 105 | >100 | 47.43 | 75.66 | 33.65 | 2.95 | 9.67 | >100 |

TABLE 9

Time-Dependent Inactivation (TDI) assessment

| Compound | $K_I$ (μM) | $k_{inact}$ (min$^{-1}$) | $k_{inact}/K_I$ (μM$^{-1}$·min$^{-1}$) |
|---|---|---|---|
| 1 | 6.4 (3.3**) | 0.0277 | 0.0043 |
| 105 | 10.2 | 0.0214 | 0.0021 |
| 2 | 22.3 | 0.0376 | 0.0017 |

As shown in Table 8 above, Compounds 1 and 2 exhibited no significant reversible inhibition; and Compound 105 exhibited potentially significant inhibition of CYP2D6 and CYP3A4 (midazolam). Also, as shown in Table 9 above, all of Compounds 1, 2, and 105 showed time-, concentration-, and NADPH-dependent inactivation of CYP3A4/5 (using midazolam as probe).

The entire disclosure of each of the patent documents and scientific articles referred to herein is incorporated by reference for all purposes.

The invention can be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

What is claimed is:

1. A method comprising administering to a subject in need thereof

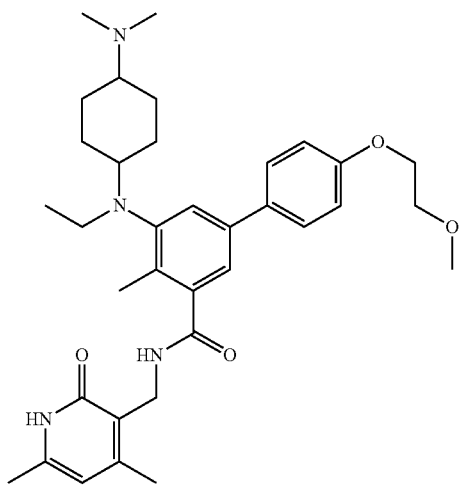

or
   a pharmaceutically acceptable salt thereof at a dosage ranging from about 0.01 mg/kg per day to about 5000 mg/kg per day.

2. The method of claim 1, wherein the subject has been diagnosed or identified as having cancer or a precancerous condition.

3. The method of claim 2, wherein the cancer is lymphoma, malignant rhabdoid tumor, a hematological cancer, leukemia, or melanoma.

4. The method of claim 3, wherein the lymphoma is selected from diffuse large B-cell lymphoma (DLBCL), non-Hodgkin's lymphoma (NHL), and follicular lymphoma.

5. The method of claim 2, wherein the cancer is malignant rhabdoid tumor.

6. The method of claim 1, wherein the compound is

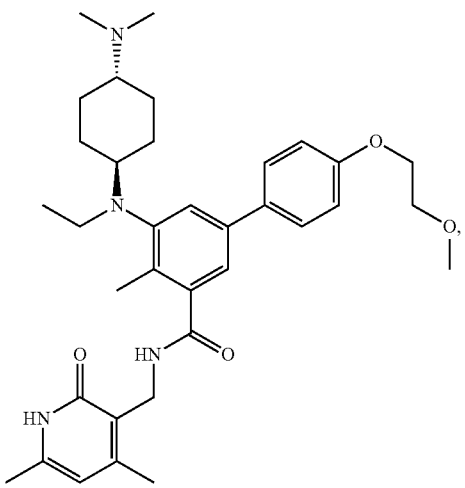

or a pharmaceutically acceptable salt thereof.

7. The method of claim 1, wherein the subject is human or non-human mammal.

8. The method of claim 7, wherein the non-human mammal is a primate, dog, cow, or pig.

9. The method of claim 1, wherein the subject is a dog.

10. A method comprising administering to a subject in need thereof

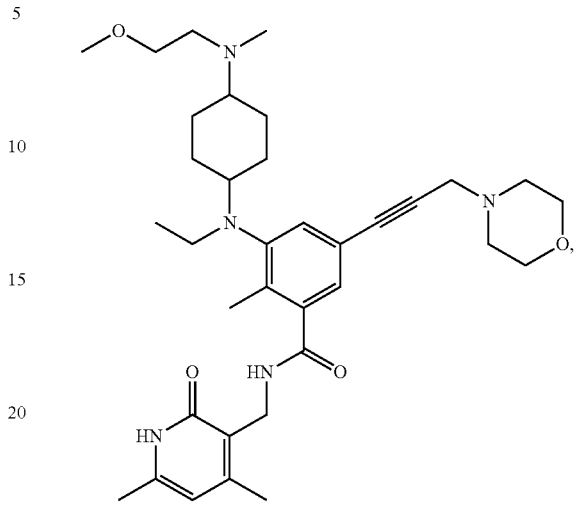

or
   a pharmaceutically acceptable salt thereof at a dosage ranging from about 0.01 mg/kg per day to about 5000 mg/kg per day.

11. The method of claim 10, wherein the subject has been diagnosed or identified as having cancer or a precancerous condition.

12. The method of claim 11, wherein the cancer is lymphoma, malignant rhabdoid tumor, a hematological cancer, leukemia, or melanoma.

13. The method of claim 12, wherein the lymphoma is selected from diffuse large B-cell lymphoma (DLBCL), non-Hodgkin's lymphoma (NHL), and follicular lymphoma.

14. The method of claim 11, wherein the cancer is malignant rhabdoid tumor.

15. The method of claim 10, wherein the subject is human or non-human mammal.

16. The method of claim 15, wherein the non-human mammal is a primate, dog, cow, or pig.

17. The method of claim 10, wherein the subject is a dog.

18. A method comprising administering to a subject in need thereof

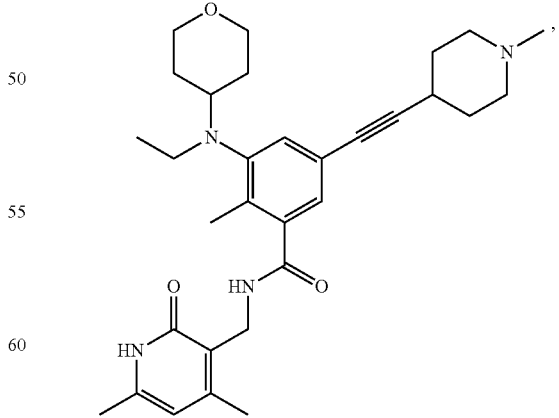

or
   a pharmaceutically acceptable salt thereof at a dosage ranging from about 0.01 mg/kg per day to about 5000 mg/kg per day.

19. The method of claim 18, wherein the subject has been previously diagnosed or identified as having cancer or a precancerous condition.

20. The method of claim 19, wherein the cancer is lymphoma, malignant rhabdoid tumor, a hematological cancer, leukemia, or melanoma.

21. The method of claim 20, wherein the lymphoma is selected from diffuse large B-cell lymphoma (DLBCL), non-Hodgkin's lymphoma (NHL), and follicular lymphoma.

22. The method of claim 18, wherein the cancer is malignant rhabdoid tumor.

23. The method of claim 18, wherein the subject is human or non-human mammal.

24. The method of claim 23, wherein the non-human mammal is a primate, dog, cow, or pig.

25. The method of claim 18, wherein the subject is a dog.

\* \* \* \* \*

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```